United States Patent
Nebolsin et al.

(10) Patent No.: US 10,745,414 B2
(45) Date of Patent: Aug. 18, 2020

(54) CRYSTAL SALT FORM OF 2,2-DIMETHYL-6-((4-((3,4,5-TRIMETHOXYPHENYL)AMINO)-1,3,5-TRIAZINE-2-YL)AMINO)-2H-PYRIDO[3,2-B][1,4]OXAZINE-3(4H)-ONE FOR HUMAN USE

(71) Applicant: LIMITED "MOLECULAR TECHNOLOGIES", Moscow (RU)

(72) Inventors: Vladimir Evgenievich Nebolsin, Borzye (RU); Fedor Nikolaevich Novikov, Moscow (RU); Germes Grigorievich Chilov, Krasnodar (RU); Oleg Valentinovich Stroganov, Moskovsky (RU); Viktor Sergeevich Stroilov, Moscow (RU); Ilya Yurievich Titov, Moscow (RU)

(73) Assignee: LIMITED "MOLECULAR TECHNOLOGIES", Moscow (RU)

( * ) Notice: Subject to any disclaimer, the term of this patent is extended or adjusted under 35 U.S.C. 154(b) by 0 days.

(21) Appl. No.: 16/301,148

(22) PCT Filed: May 10, 2017

(86) PCT No.: PCT/RU2017/050037
§ 371 (c)(1),
(2) Date: Nov. 13, 2018

(87) PCT Pub. No.: WO2017/196210
PCT Pub. Date: Nov. 16, 2017

(65) Prior Publication Data
US 2019/0292198 A1    Sep. 26, 2019

(30) Foreign Application Priority Data
May 13, 2016  (RU) .............................. 2015147258

(51) Int. Cl.
*A61K 31/5383*   (2006.01)
*C07D 498/04*    (2006.01)

(52) U.S. Cl.
CPC ........ *C07D 498/04* (2013.01); *C07B 2200/13* (2013.01)

(58) Field of Classification Search
CPC ............ A61K 31/5365; A61K 31/5383; C07D 498/04
USPC ....................... 514/230.5; 544/105
See application file for complete search history.

(56) References Cited

FOREIGN PATENT DOCUMENTS

RU         2 509 770        3/2014
WO    WO 2007/124221      11/2007

OTHER PUBLICATIONS

Zeifman, et. al, Mendeleev Commun., 2012, 22, 73-74.*
Bastin et. al. Organic Process Research & Development 2000, 4, 427-435.*
Stahl, et. al. Handbook of Pharmaceutical Salts, Properties, Selection, and Use, (2002), 1-374.*
International Search Report issued in PCT/RU2017/050037 dated Sep. 14, 2017.
Berge et al., "Pharmaceutical Salts" *Pharmaceutical Sciences*, vol. 66, No. 1, Jan. 1977, pp. 1-19.
Hannon et al., "Effects of the Src Kinase Inhibitor Saracatinib (AZD0530) on Bone Turnover in Healthy Men: A Randomized, Double-Blind, Placebo-Controlled, Multiple-Ascending-Dose Phase I Trial" *Journal of Bone and Mineral Research*, vol. 25, No. 3, Mar. 2010, pp. 463-471.
Rakitina et al., "Efficacy of novel Syk-kinase inhibitors MT-SYK-03 and MT-SKY-322 in cellular models of autoimmunity and cancer" *Mendeleev Commun.*, 2012, 22, 287-289.
Verbeeck et al. "Generic substitution: The use of medicinal products containing different salts and implications for safety and efficacy" *European Journal of Pharmaceutical Sciences* 28 (2006) pp. 1-6.
Yanagi et al., "Syk Expression and Novel Function in a Wide Variety of Tissues" *Biochemical and Biophysical Research Communications*, 288, 495-498 (2001).

* cited by examiner

Primary Examiner — Jeffrey H Murray
(74) Attorney, Agent, or Firm — Nixon & Vanderhye P.C.

(57) ABSTRACT

The invention is relevant to chemistry of organic compounds, pharmacology and medicine, and is related to prevention and treatment of musculoskeletal diseases in human and animals associated with the disorder of bone and/or cartilage metabolism, particularly with such musculoskeletal diseases as osteoporosis, osteoarthritis and osteochondrosis, using a new salt form of 2,2-dimethyl-6-((4-((3,4,5-trimethoxyphenyl)amino)-1,3,5-triazine-2-yl)amino)-2H-pyrido[3,2-b][1,4]oxazine-3(4H)-one. A salt of this compound with 4-methylbenzenesulfonic acid

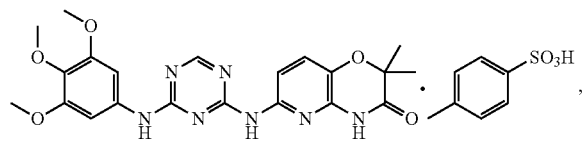

including its hydrates, solvates and polymorphic modifications of the salt, hydrates and solvates is featured with acceptable pharmacokinetic parameters and increased efficiency in the inhibition of Src-family kinases and Syk kinase, as well as other therapeutically significant kinases. This invention also covers pharmaceutical compositions containing therapeutically effective amount of the salt according to the invention.

8 Claims, 22 Drawing Sheets

| Code | Amount of primary base, mg | Solvent | Solvent volume, ml | Acid | Number of acid equivalents | Dissolution at heating | Dissolution after acid addition | Precipitation after acid addition | Precipitation at cooling |
|---|---|---|---|---|---|---|---|---|---|
| 1 | 2 | 3 | 4 | 5 | 6 | 7 | 8 | 9 | 10 |
| S-2-1-B-TSA | 107 | n-butanol | 11.0 | pTSA | 1.05 | - | + | - | + |
| S-2-2-C2-TSA | 102 | ethanol | 10.0 | pTSA | 1.05 | - | - | N/A | N/A |
| S-2-3-T-TSA | 101 | THF | 10.0 | pTSA | 1.05 | - | - | N/A | N/A |
| S-2-4-D-TSA | 98 | dioxane | 7.0 | pTSA | 1.05 | + | N/A | + | N/A |
| S-2-5-A1-TSA | 98 | acetone | 10.0 | pTSA | 1.05 | - | + | + | N/A |
| S-2-6-B-MA | 94 | n-butanol | 9.5 | Maleic acid | 1.05 | - | - | - | N/A |
| S-2-7-C2-MA | 108 | ethanol | 11.0 | Maleic acid | 1.05 | - | - | N/A | N/A |
| S-2-8-T-MA | 108 | THF | 11.0 | Maleic acid | 1.05 | - | - | N/A | N/A |
| S-2-9-D-MA | 104 | dioxane | 7.3 | Maleic acid | 1.05 | + | N/A | - | N/A |
| S-2-10-A1-MA | 90 | acetone | 9.0 | Maleic acid | 1.05 | - | - | N/A | N/A |
| S-2-11-B-HBr | 105 | n-butanol | 10.5 | HBr | 1.05 | - | + | + | N/A |
| S-2-12-C2-HBr | 93 | ethanol | 9.3 | HBr | 1.05 | - | - | N/A | N/A |
| S-2-13-T-HBr | 107 | THF | 10.7 | HBr | 1.05 | + | N/A | + | N/A |
| S-2-14-D-HBr | 91 | dioxane | 6.4 | HBr | 1.05 | - | - | N/A | N/A |
| S-2-15-A1-HBr | 105 | acetone | 10.5 | HBr | 1.05 | - | + | + | N/A |
| S-2-16-A1-HCl | 95 | acetone | 9.5 | HCl | 1.05 | - | - | N/A | N/A |
| S-2-17-B-HCl | 108 | n-butanol | 10.8 | HCl | 1.05 | - | + | + | N/A |
| S-2-18-C2-HCl | 98 | ethanol | 9.8 | HCl | 1.05 | - | + | + | N/A |

Figure 1

| 1 | 2 | 3 | 4 | 5 | 6 | 7 | 8 | 9 | 10 |
|---|---|---|---|---|---|---|---|---|---|
| S-2-19-T-HCl | 103 | THF | 10.3 | HCl | 1.05 | - | - | N/A | N/A |
| S-2-20-D-HCl | 104 | dioxane | 7.3 | HCl | 1.05 | + | N/A | + | N/A |
| S-2-21-B-PA | 98 | n-butanol | 9.8 | H₃PO₄ | 1.05 | - | - | N/A | N/A |
| S-2-22-C2-PA | 92 | ethanol | 9.2 | H₃PO₄ | 1.05 | - | - | N/A | N/A |
| S-2-23-T-PA | 96 | THF | 9.6 | H₃PO₄ | 1.05 | - | - | N/A | N/A |
| S-2-24-D-PA | 106 | dioxane | 7.4 | H₃PO₄ | 1.05 | + | N/A | - | - |
| S-2-25-A1-PA | 106 | acetone | 10.6 | H₃PO₄ | 1.05 | - | - | N/A | N/A |
| S-2-26-B-CSA | 102 | n-butanol | 10.2 | Camphorsulfonic acid | 1.05 | - | + | - | + |
| S-2-27-C2-CSA | 106 | ethanol | 10.6 | Camphorsulfonic acid | 1.05 | - | - | N/A | N/A |
| S-2-28-T-CSA | 97 | THF | 9.7 | Camphorsulfonic acid | 1.05 | - | - | N/A | N/A |
| S-2-29-D-CSA | 98 | dioxane | 6.9 | Camphorsulfonic acid | 1.05 | + | N/A | - | + |
| S-2-30-A1-CSA | 100 | acetone | 10.0 | Camphorsulfonic acid | 1.05 | - | - | N/A | N/A |
| S-2-46-C2-FA | 105 | ethanol | 10.5 | Fumaric acid | 1.05 | - | - | N/A | N/A |
| S-2-47-T-FA | 110 | THF | 10.6 | Fumaric acid | 1.05 | - | - | N/A | N/A |
| S-2-48-B-FA | 107 | n-butanol | 10.7 | Fumaric acid | 1.05 | - | - | N/A | N/A |
| S-2-31-A1-SA | 110 | acetone | 11.0 | H₂SO₄ | 1.05 | - | - | N/A | N/A |
| S-2-32-B-SA | 110 | n-butanol | 11.0 | H₂SO₄ | 1.05 | - | + | - | + |
| S-2-33-C2-SA | 96 | ethanol | 9.6 | H₂SO₄ | 1.05 | - | - | N/A | N/A |
| S-2-34-T-SA | 96 | THF | 9.6 | H₂SO₄ | 1.05 | - | - | N/A | N/A |

Figure 1 (continued)

| 1 | 2 | 3 | 4 | 5 | 6 | 7 | 8 | 9 | 10 |
|---|---|---|---|---|---|---|---|---|---|
| S-2-35-D-SA | 94 | dioxane | 6.6 | $H_2SO_4$ | 1.05 | + | N/A | + | N/A |
| S-2-36-B-hSA | 105 | n-butanol | 10.4 | $H_2SO_4$ | 0.52 | - | + | - | + |
| S-2-37-C2-hSA | 114 | ethanol | 11.4 | $H_2SO_4$ | 0.52 | - | - | N/A | N/A |
| S-2-38-T-hSA | 93 | THF | 9.3 | $H_2SO_4$ | 0.52 | - | - | N/A | N/A |
| S-2-39-D-hSA | 116 | dioxane | 8.1 | $H_2SO_4$ | 0.52 | + | N/A | + | N/A |
| S-2-40-A1-hSA | 113 | acetone | 11.3 | $H_2SO_4$ | 0.52 | - | - | N/A | N/A |
| S-2-41-A1-MSA | 103 | acetone | 10.3 | Methanesulfonic acid | 1.05 | - | - | N/A | N/A |
| S-2-42-T-MSA | 100 | THF | 10.0 | Methanesulfonic acid | 1.05 | - | - | N/A | N/A |
| S-2-43-D-MSA | 114 | dioxane | 8.0 | Methanesulfonic acid | 1.05 | + | N/A | + | N/A |
| S-2-44-B-MSA | 106 | n-butanol | 10.6 | Methanesulfonic acid | 1.05 | - | + | - | + |
| S-2-45-C2-MSA | 100 | ethanol | 10.0 | Methanesulfonic acid | 1.05 | - | - | N/A | N/A |
| S-2-46-C2-CA | 105 | ethanol | 10.5 | Citric acid | 1.05 | - | - | N/A | N/A |
| S-2-47-T-CA | 110 | THF | 10.6 | Citric acid | 1.05 | - | - | N/A | N/A |
| S-2-48-B-CA | 107 | n-butanol | 10.7 | Citric acid | 1.05 | - | - | N/A | N/A |

Figure 1 (continued)

| Code | Amount of base, mg | Solvent | Solvent volume, ml | Acid | Number of acid equivalents | Dissolution | | Precipitation | | Filterability | XRD results |
|---|---|---|---|---|---|---|---|---|---|---|---|
| | | | | | | at heating | after acid addition | after acid addition | at cooling | | |
| S-3-1-B-TSA | 2,130 | n-butanol | 210.3 | pTSA | 1.05 | - | + | - | + | + | Polycrystal |
| S-3-2-B-HBr | 2,150 | n-butanol | 100.8 | HBr | 1.05 | - | - | + | N/A | + | Polycrystal |
| S-3-3-B-CSA | 1,980 | n-butanol | 90.9 | Camphorsulfonic acid | 1.05 | - | partial | - | + | - | N/A |
| S-3-4-B-HCl | 1,900 | n-butanol | 90.5 | HCl | 1.05 | - | - | + | N/A | + | Polycrystal |
| S-3-5-B-hSA | 2,020 | n-butanol | 200.2 | H₂SO₄ | 0.52 | - | + | - | + | - | N/A |
| S-3-6-B-SA | 1,900 | n-butanol | 190.0 | H₂SO₄ | 1.05 | - | partial | - | + | - | N/A |
| S-3-7-B-MSA | 2,140 | n-butanol | 210.4 | Methanesulfonic acid | 1.05 | - | + | - | + | - | N/A |
| S-3-8-B-HBr | 2,020 | n-butanol | 200.2 | HBr | 1.05 | - | partial | + | N/A | + | Polycrystal |
| S-3-9-B-CSA | 2,000 | n-butanol | 200.0 | Camphorsulfonic acid | 1.05 | - | + | - | + | + | Polycrystal |
| S-3-10-B-HCl | 1,920 | n-butanol | 190.2 | HCl | 1.05 | - | partial | + | N/A | + | Crystal |
| S-3-11-C2-HCl | 2,150 | ethanol | 210.5 | HCl | 1.05 | + | partial | + | N/A | + | Crystal |
| S-3-12-A1-TSA | 2,160 | acetone | 210.6 | pTSA | 1.05 | + | partial | + | N/A | + | Crystal |
| S-3-13-D-HCl | 2,100 | dioxane | 140.7 | HCl | 1.05 | + | N/A | - | N/A | - | N/A |
| S-3-14-D-CSA | 1,910 | dioxane | 130.4 | Camphorsulfonic acid | 1.05 | + | N/A | + | + | - | N/A |
| S-3-15-D-hSA | 2,170 | dioxane | 150.2 | H₂SO₄ | 1.05 | + | N/A | + | N/A | - | N/A |
| S-3-16-D-SA | 2,150 | dioxane | 150.1 | H₂SO₄ | 0.52 | + | N/A | + | N/A | + | Polycrystal |
| S-3-17-D-MSA | 2,060 | dioxane | 140.4 | Methanesulfonic acid | 1.05 | + | N/A | + | N/A | + | Amorphous |
| S-3-18-D-HBr | 1,970 | dioxane | 130.8 | HBr | 1.05 | + | N/A | + | N/A | - | N/A |
| S-3-19-D-TSA | 2,190 | dioxane | 150.3 | pTSA | 1.05 | + | N/A | + | N/A | - | N/A |

Figure 2

| Sample code | Structure | Molecular formula | Calculated | | Found | |
|---|---|---|---|---|---|---|
| 1 | 2 | 3 | 4 | 5 | 6 | |
| S3-0 | (structure) | C₂₁H₂₃N₇O₅ | C | 55.62 | 55.49 / 55.51 | |
| | | | H | 5.11 | 5.16 / 5.19 | |
| | | | N | 21.62 | 21.90 / 21.74 | |
| S3-1-B-TSA<br>S3-12-A1-TSA | (structure) Polymorphic modification A | C₂₈H₃₁N₇O₈S | C | 53.75 (52.25) | 51.99 / 52.13 | 52.09 / 51.92 |
| | | | H | 4.99 (5.17) | 5.29 / 5.19 | 5.23 / 5.43 |
| | | | N | 15.67 (15.23) | 15.04 / 15.12 | 15.23 / 15.14 |
| | | | S | 5.13 | | |
| SYK 91/1 | (structure) Polymorphic modification B | C₂₈H₃₁N₇O₈S | C | 53.75 (52.25) | | 52.19 / 52.21 |
| | | | H | 4.99 (5.17) | | 5.21 / 5.19 |
| | | | N | 15.67 (15.23) | | 15.13 / 15.18 |
| | | | S | 5.13 | | |
| S3-2-B-HBr<br>S3-8-B-HBr | (structure) · HBr | C₂₁H₂₄BrN₇O₅ | C | 47.20 | 48.02 / 48.14 | 47.00 / 47.09 |
| | | | H | 4.53 | 4.62 / 4.67 | 4.57 / 4.59 |
| | | | Br | 14.95 | | |
| | | | N | 18.35 | 18.80 / 18.93 | 18.40 / 18.38 |
| S3-9-B-CSA | (structure) | C₃₁H₃₉N₇O₉S | C | 54.30 | | 51.98 / 52.26 |
| | | | H | 5.73 | | 6.02 / 6.02 |
| | | | N | 14.30 | | 14.05 / 14.20 |
| | | | S | 4.68 | | |

Figure 3

| 1 | 2 | 3 | 4 | 5 | 6 | |
|---|---|---|---|---|---|---|
| S3-17-D-MSA | (structure) | $C_{22}H_{27}N_7O_8S$ | C | 48.08 (46.56) | 46.35 / 46.47 | |
| | | | H | 4.95 (5.15) | 5.25 / 5.21 | |
| | | | N | 17.84 (17.28) | 16.23 / 16.25 | |
| | | | S | 5.83 | | |
| S3-4-B-HCl S3-10-B-HCl S3-11-C2-HCl | (structure) | $C_{21}H_{24}ClN_7O_5$ | C | 51.48 (49.66) | 48.65 / 48.76 | 50.15 / 49.88 | 49.15 / 49.04 |
| | | | H | 4.94 (5.16) | 4.95 / 5.01 | 5.05 / 5.05 | 5.06 / 5.03 |
| | | | Cl | 7.27 | | | |
| | | | N | 20.01 (19.30) | 19.06 / 19.09 | 19.61 / 19.46 | 19.25 / 19.29 |
| S3-16-D-SA | (structure) | $C_{42}H_{48}N_{14}O_{14}S$ | C | 50.19 | | 55.02 / 54.86 | |
| | | | H | 4.81 | | 5.31 / 5.55 | |
| | | | N | 19.51 | | 20.00 / 20.28 | |
| | | | S | 3.19 | | | |

Figure 3 (continued)

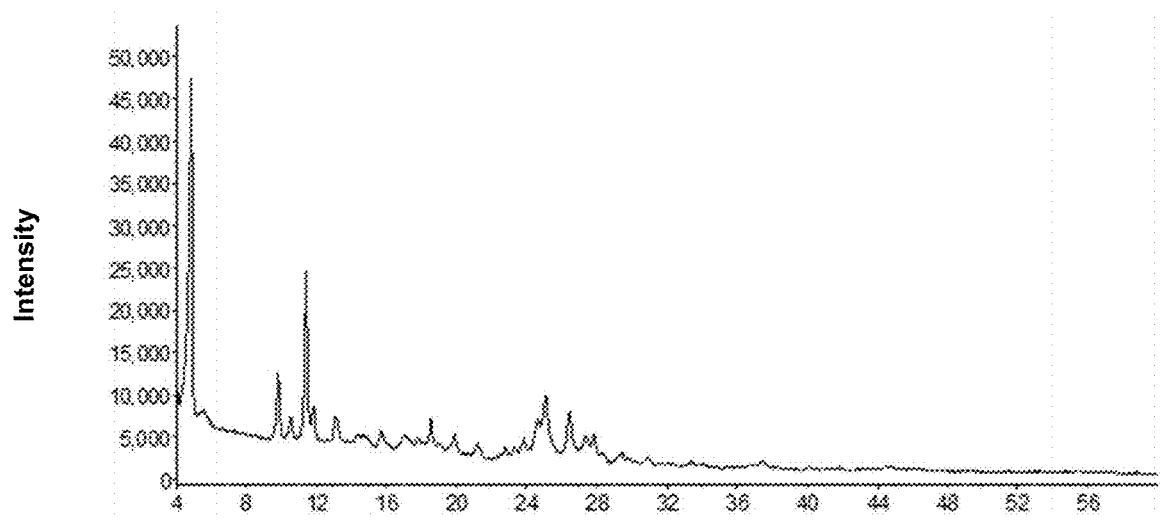
a)
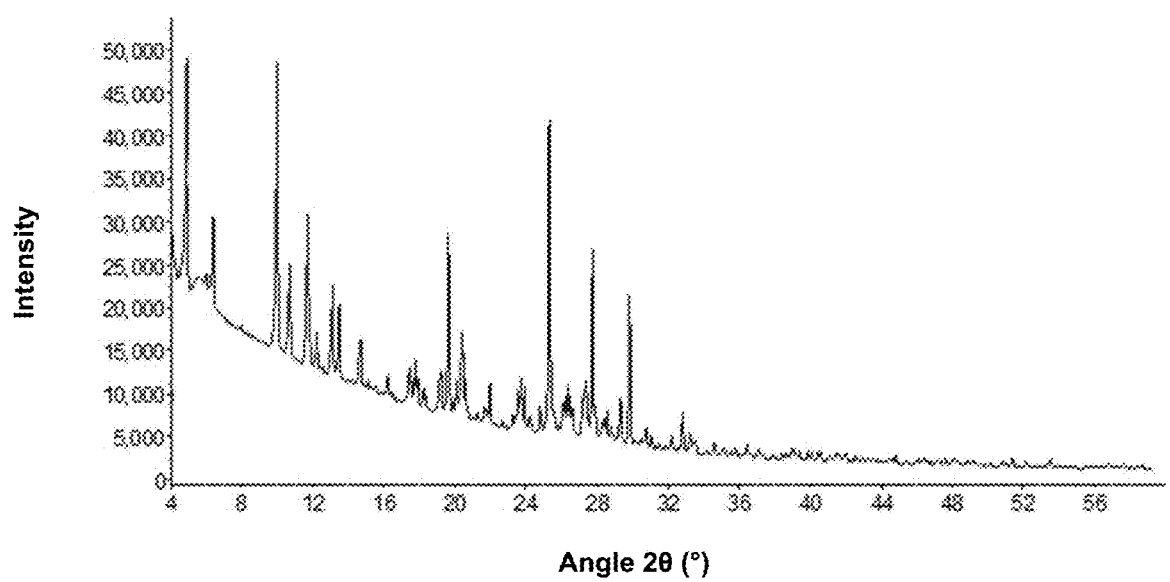
b)
Figure 4

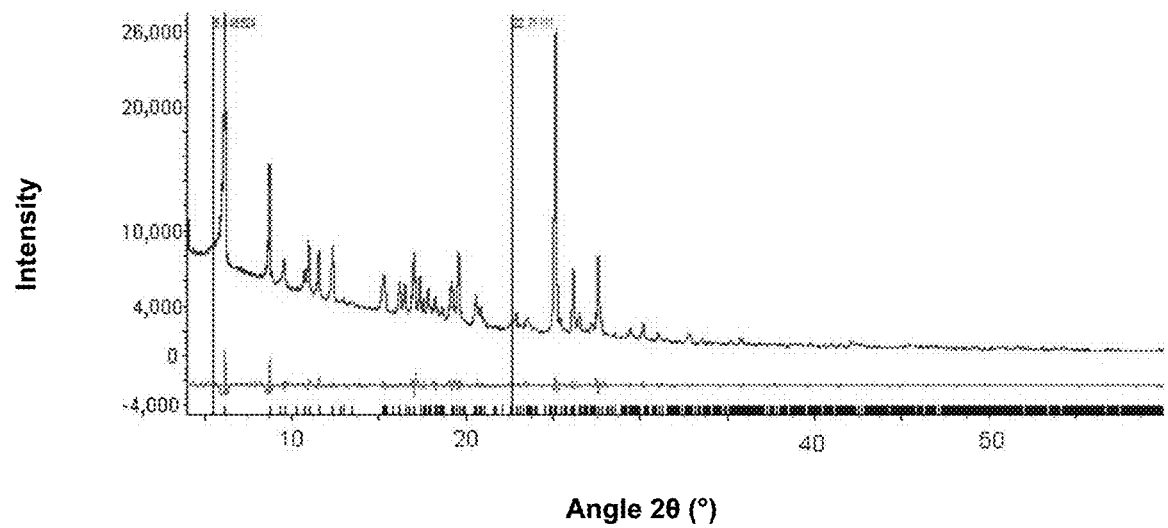
a)
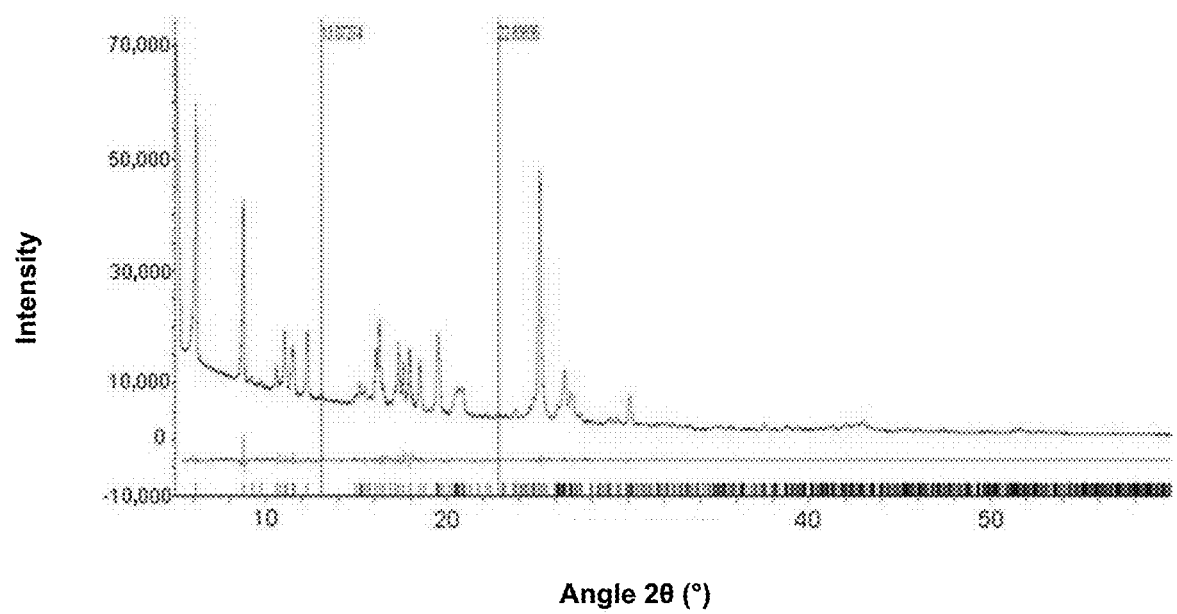
b)
Figure 9

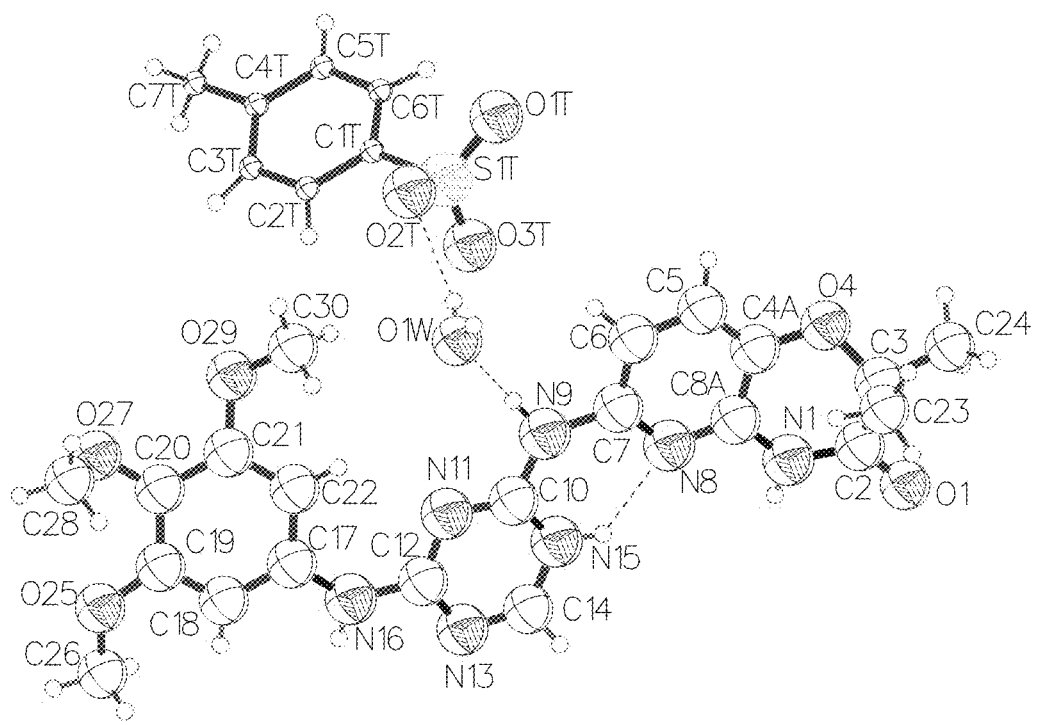
a)
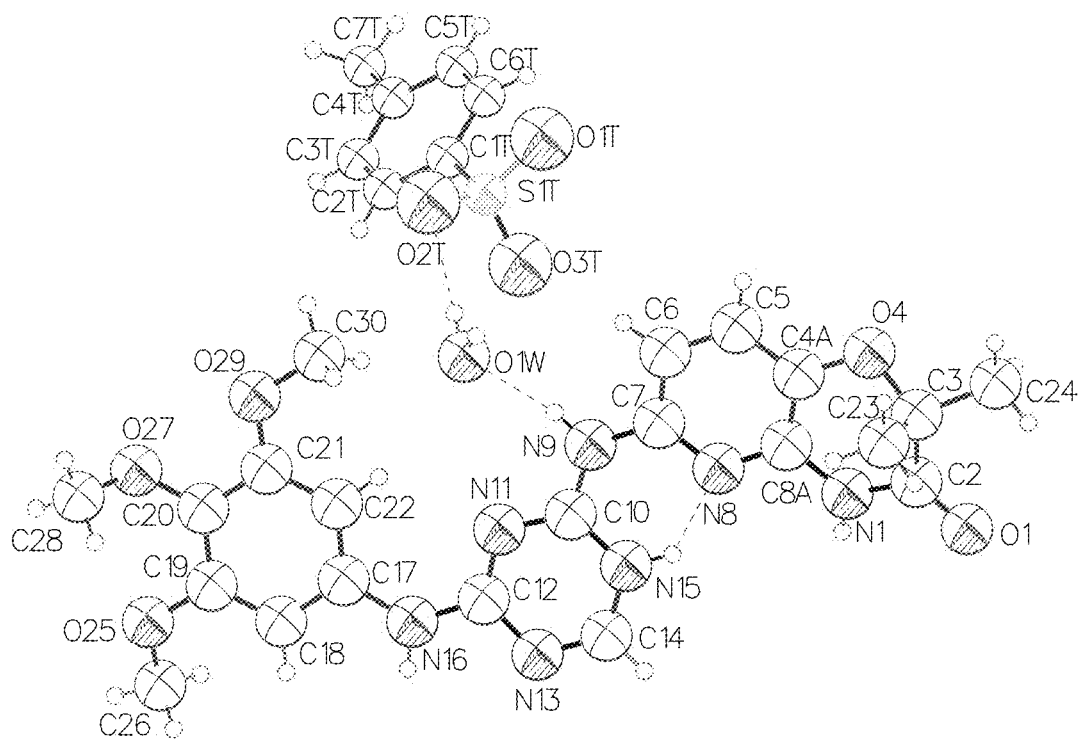
b)
Figure 11 a)

b)

a)

b)

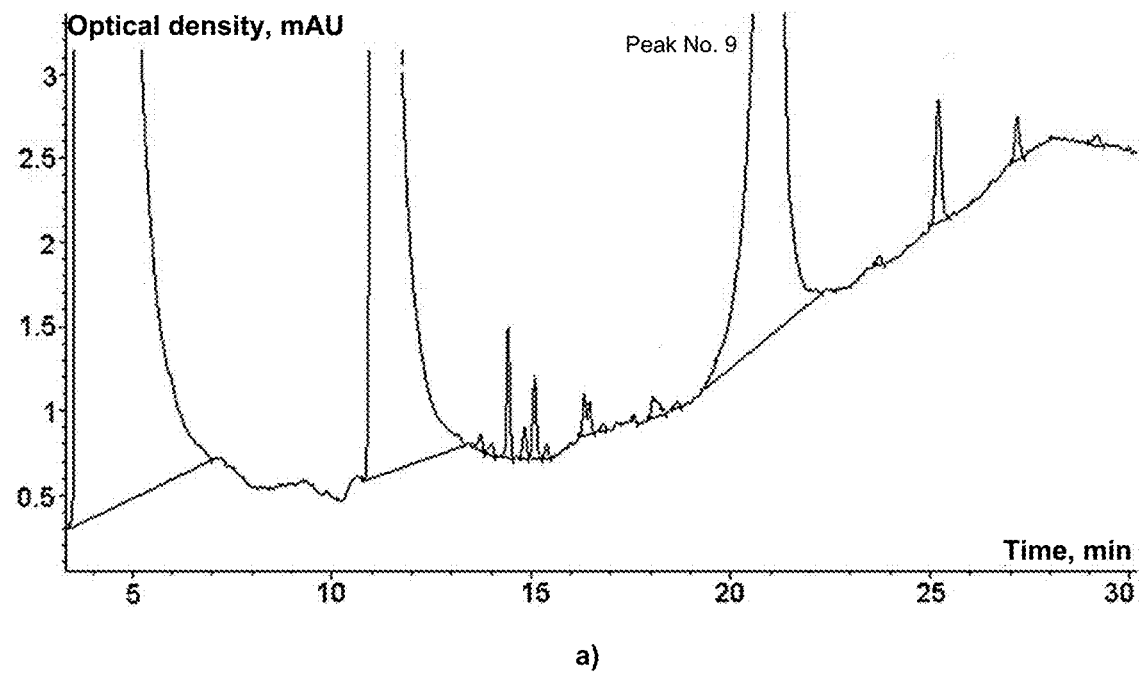
a)
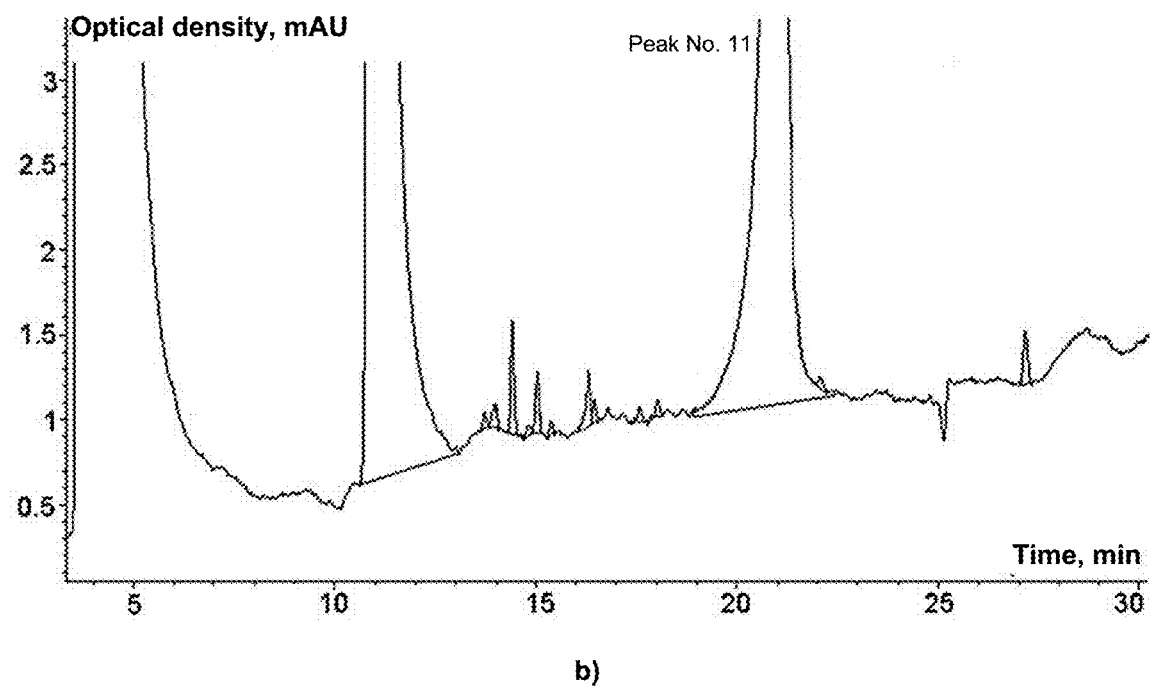
b)
Figure 17

CRYSTAL SALT FORM OF 2,2-DIMETHYL-6-((4-((3,4,5-TRIMETHOXYPHENYL)AMINO)-1,3,5-TRIAZINE-2-YL)AMINO)-2H-PYRIDO [3,2-B][1,4]OXAZINE-3(4H)-ONE FOR HUMAN USE

This application is the U.S. national phase of International Application No. PCT/RU2017/050037 filed May 10, 2017, which designated the U.S. and claims priority to RU Patent Application No. 2015147258 filed May 13, 2016, the entire contents of each of which are hereby incorporated by reference.

TECHNICAL FIELD

This invention is relevant to chemistry of organic compounds, pharmacology and medicine, namely to a salt form of compound as well as to its crystal (polymorphic) form promising for treatment of musculoskeletal diseases related to the disorder of bone and/or cartilage metabolism, particularly of osteoporosis, osteoarthritis and osteochondrosis.

BACKGROUND OF THE INVENTION

A problem of an increasing incidence rate of such musculoskeletal diseases as osteoporosis, osteoarthritis, and osteochondrosis is becoming increasingly relevant. This is reflected by numerous publications devoted to this subject. Despite of efforts being taken by experts in different areas, this problem is far from being resolved.

Osteoporosis is the most common human bone disease. This is a chronic systemic disease characterized by lowering bone mass and progressing deterioration of bone tissue microarchitecture, which can lead to decreased bone strength and increased risk of pathologic fracture. Now, osteoporosis is classified into two basic types which are primary and secondary one. Drugs used for osteoporosis treatment are bone resorption inhibitors (estrogens, selective estrogen receptor modulators, selective tissue estrogenic activity regulators, calcitonins, bisphosphonates and other drugs (odanacatib, denosumab, etc.)); osteogenesis stimulators (fluorides, somatotropic hormone, anabolic steroids, androgens); multifunctional drugs (strontium ranelate, active metabolites of ergocalciferol, ossein-hydroxyapatite compound).

Problem of the osteoporosis treatment is still of topic issue despite the wide range of approved drugs. Severe adverse reactions induced by prolonged drug administration and poor compliance to prolonged treatment are the major disadvantages of the existing treatment.

Osteoarthritis (OA) is considered an organ lesion, i.e, an entire joint disorder when a pathological process involves all the joint components: cartilage, subchondral bone plate, synovial membrane, ligaments, capsule, and muscles.

Osteoarthritis treatment is still seeking to resolve the disease symptoms, i.e., pain relief, improving the joint functionality and arresting the pathology progression. A symptomatic effect is achieved by a combination of non-pharmacological and pharmacological methods set out in numerous guidelines. In most cases, the existing treatment methods do not achieve joint tissue neogenesis, arrest of pathology progression or at least long-term and steady slowdown in the disease progression.

Thus, we need to develop new effective drugs along with other methods of treatment for musculoskeletal diseases related to the disorder of bone and/or cartilage metabolism such as osteoporosis, osteoarthritis, and osteochondrosis. Modulation of intracellular signaling pathways is considered to be one of the most interesting trends.

Protein kinases are protein family critical for regulation of key cellular processes; disorders in activity of these proteins can result in various diseases. A promising approach to treatment of diseases associated with abnormal activity of protein kinases is using low-molecular weight compounds to inhibit activity thereof. Examples of such inhibitors approved for clinical practice are: imatinib, nilotinib, dasatinib, sunitinib, sorafenib, lapatinib, gefitinib, erlotinib, crizotinib. Lots of drug candidates being kinase inhibitors are under clinical trial stage or preclinical stage now.

c-Src kinase (Proto-oncogene tyrosine-protein kinase) is a non-receptor tyrosine kinase involved in processes of embryogenesis and cell growth. Inhibition of c-Src kinase was demonstrated to block actin ring formation and prevent osteoclast-mediated bone destruction in various in vitro models. Furthermore, c-Src kinase is involved in signaling pathway leading to hypertrophic changes in chondrocytes associated with aberrant cartilage metabolism, which is characteristic for diseases related to dystrophic degeneration processes in this tissue.

It has been demonstrated earlier, that saracatinib is a new competitive inhibitor of Src kinase, which inhibits resorption of bone tissue in vitro. In the course of phase I clinical trials, it was established that saracatinib inhibits osteoclast-mediated resorption of bone tissue in healthy men without any adverse events (R. A. Hannon, G. Clack, M. Rimmer et al. Effects of the Src kinase inhibitor saracatinib (AZD0530) on bone turnover in healthy men: a randomized, double-blind, placebo-controlled, multiple ascending dose phase I trial.//J Bone Miner Res. 2010. V. 25. No. 3. P. 463-71.). However the further clinical trials showed that high toxicity of saracatinib at daily exposure of a therapeutically effective dose makes it impossible to use this drug in clinical practice for the musculoskeletal disease treatment.

Thus, inhibition of c-Src kinase is a highly promising strategy of managing osteoporosis, osteoarthritis and other musculoskeletal diseases, which pathogenesis is related to the bone and cartilage aberrant metabolism.

However, drugs based on Src kinase inhibitors are not available now in the clinical practice of musculoskeletal disease treatment. Thus, a task arises to research and develop new effective drugs, i.e., c-Src kinase inhibitors, for treatment of osteoporosis, osteoarthritis and other musculoskeletal diseases.

DISCLOSURE OF INVENTION

An object of this invention is the development of a new drug with acceptable pharmacokinetics for effective musculoskeletal disease treatment, particularly for treatment of osteoporosis and osteoarthritis.

A technical result of this invention is the development and preparation of an effective kinase inhibitor, particularly c-Src kinase inhibitor, with high inhibitory activity, and pharmacokinetic parameters, particularly high maximum and average daily concentration as well as high value of $AUC_\infty$ (area under concentration-time curve) in animal and human blood, which would allow using this inhibitor for treatment of diseases related to aberrant kinase activity resulting in disorder of bone and cartilage metabolism, i.e., using for treatment of musculoskeletal diseases, particularly osteoarthritis and osteoporosis.

An additional technical result is the development and preparation of a kinase inhibitor, particularly c-Src kinase inhibitor, featuring easy scalable process of production and purification as well as high purity of the obtained product with minimum number of produced compound purification stages.

The specified technical result is achieved by producing a salt of 4-methylbenzenesulfonic acid and 2,2-dimethyl-6-((4-((3,4,5-trimethoxyphenyl)amino)-1,3,5-triazine-2-yl)amino)-2H-pyrido[3,2-b][1,4]oxazine-3(4H)-one base

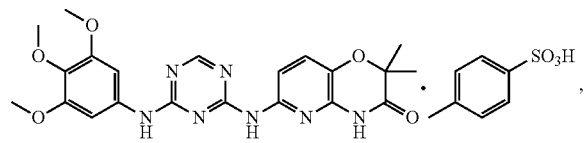

or salt hydrate, solvate as well as polymorphic modifications capable to inhibit aberrant activity of Src-family kinases, particularly c-Src kinase and Syk kinase.

In particular embodiments of the invention, the salt of 4-methylbenzenesulfonic acid and 2,2-dimethyl-6-((4-((3,4,5-trimethoxyphenyl)amino)-1,3,5-triazine-2-yl)amino)-2H-pyrido[3,2-b][1,4]oxazine-3(4H)-one base is a hydrate as well as polymorphic modifications thereof.

Particular embodiments of the invention imply a monohydrate of 4-methylbenzenesulfonic acid and 2,2-dimethyl-6-((4-((3,4,5-trimethoxyphenyl)amino)-1,3,5-triazine-2-yl)amino)-2H-pyrido[3,2-b][1,4]oxazine-3(4H)-one base as well as polymorphic modifications thereof.

One of the most preferable embodiments of the invention is a polymorphic modification of the monohydrate of 4-methylbenzenesulfonic acid and 2,2-dimethyl-6-((4-(3,4,5-trimethoxyphenyl)amino)-1,3,5-triazine-2-yl)amino)-2H-pyrido[3,2-b][1,4]oxazine-3(4H)-one base, which is a crystal phase with the following parameters of a unit cell determined by a method of X-ray powder diffraction (XRD) at 25±5° C. using CuKα1-radiation with a wavelength of 1.5406 Å, equal to a=10.98±0.05 Å, b=28.48±0.05 Å, c=10.60±0.05 Å, β=113.7±0.1°, and with volume of V=3,037.5±0.5 Å$^3$. Space group P2$_1$/c. Positions of intrinsic peaks at a Debye diffraction pattern of this polymorphic modification (2θ): 6.2; 8.8; 9.6; 10.7; 11.0; 11.6; 12.4; 15.3; 16.2; 16.5; 17.0; 17.4; 17.6; 17.9; 18.3; 18.6; 19.3; 19.3; 19.6; 20.6; 20.9; 23.5; 25.2; 26.2; 26.5; 27.2; 27.6; 30.2.

Another preferable embodiment of the invention is a polymorphic modification of the monohydrate of 4-methylbenzenesulfonic acid and 2,2-dimethyl-6-((4-((3,4,5-trimethoxyphenyl)amino)-1,3,5-triazine-2-yl)amino)-2H-pyrido[3,2-b][1,4]oxazine-3(4H)-one base, which is a crystal phase with the following parameters of a unit cell determined by XRD at 25±5° C. using CuKα1-radiation with a wavelength of 1.5406 Å, equal to a=11.09±0.05 Å, b=14.38±0.05 Å, c=10.53±0.05 Å, α=90.06°, β=114.6±0.1°, γ=91.1°, and with volume of V=1,525.9±0.5 Å$^3$. Space group P$\bar{1}$. Positions of intrinsic peaks at a Debye diffraction pattern of this polymorphic modification (2θ): 6.1; 8.8; 10.6; 11.0; 11.5; 12.3; 15.0; 15.2; 15.5; 15.8; 16.1; 16.3; 17.3; 17.6; 17.9; 18.5; 19.5; 20.5; 20.7; 20.8; 24.6; 24.8; 25.1; 26.1; 26.5; 26.9; 30.1; 43.0.

This invention also covers use of the salt or its hydrate, solvate and polymorphic modifications according to the invention as an inhibitor of an aberrant kinase activity. At that, in some embodiments of the invention, the kinase is a non-receptor protein kinase, in particular, the kinase is selected from Syk kinase or Src-family kinase. The Src-family kinase is c-Src, Yes, Fyn, Fgr, Yrk, Lyn, Blk, Hck or Lck kinase.

The specified technical result is also achieved by using the salt or its hydrate, solvate as well as polymorphic modifications according to the invention to produce a pharmaceutical composition for prevention and/or treatment of disorders related to the aberrant kinase activity. At that, in some embodiments of the invention, the kinase is a non-receptor protein kinase, in particular, the kinase is selected from Syk kinase or Src-family kinase. The Src-family kinase is c-Src, Yes, Fyn, Fgr, Yrk, Lyn, Blk, Hck or Lck kinase.

Furthermore, the invention implies pharmaceutical compositions for prevention and/or treatment of the disorder related to the aberrant kinase activity, which are featured with content of an effective amount of the salt according to the invention and, at least, one pharmaceutically acceptable auxiliary substance. In some embodiments of the invention, the auxiliary substance is a pharmaceutically acceptable carrier and/or excipient. These compositions are designed for modulating activity of kinases being non-receptor protein kinases, in particular, the kinase is selected from Syk kinase or Src-family kinase. The Src-family kinase is c-Src, Yes, Fyn, Fgr, Yrk, Lyn, Blk, Hck or Lck kinase.

The invention also includes a method of prevention and/or treatment of the disorder related to the aberrant kinase activity in the body inclusive of administration of a pharmaceutical composition according to the invention in this body. The disorder related to the aberrant kinase activity is a disease related to the disorder of bone and cartilage metabolism, particularly musculoskeletal diseases. In some open-ended embodiments of the invention, the musculoskeletal disease is osteoarthritis or osteoporosis. In particular embodiments of the invention, the body is a human or an animal. In some embodiments of the invention, the animal is a cat, dog or horse.

Achievement of the specified technical result is also provided by a method of crystallization of compounds according to the invention including the following stages:
 a. introduction of 4-methylbenzenesulfonic acid or its hydrate in an organic solvent into a suspension or a solution of 2,2-dimethyl-6-((4-((3,4,5-trimethoxyphenyl)amino)-1,3,5-triazine-2-yl)amino)-2H-pyrido[3,2-b][1,4]oxazine-3(4H)-one in organic solvent or solvent mixture; 4-methylbenzenesulfonic acid or its hydrate can be introduced both at room temperature, and at heating or cooling of each component; the reagents can also be mixed in reverse order;
 b. crystallization of the obtained salt;
 c. separating salt crystals from the solvent.

In some embodiments of the invention, the stage (a) solvent used as suspending media for 2,2-dimethyl-6-((4-((3,4,5-trimethoxyphenyl)amino)-1,3,5-triazine-2-yl)amino)-2H-pyrido[3,2-b][1,4]oxazine-3(4H)-one is acetone.

In particular embodiments of the invention, the stage (a) solvent used for dissolution of 4-methylbenzenesulfonic acid or its hydrate is ethanol.

In some embodiments of the invention, the salt is additionally re-crystallized after the stage (c).

In some other particular embodiments of the invention, a stage of crystallization initiation is additionally used when the salt is obtained from solutions. The crystallization initiation can be achieved by introducing crystals of 4-methylbenzenesulfonic acid salt and 2,2-dimethyl-6-((4-((3,4,5-trimethoxyphenyl)amino)-1,3,5-triazine-2-yl)amino)-2H-pyrido[3,2-b][1,4]oxazine-3(4H)-one base into the solution or by any other known method.

In particular embodiments of the invention, the stage (a) is preceded by an additional stage of purifying 2,2-dimethyl-6-((4-((3,4,5-trimethoxyphenyl)amino)-1,3,5-triazine-2-yl)

amino)-2H-pyrido[3,2-b][1,4]oxazine-3(4H)-one base by transforming it into a salt of sulfuric, hydrochloric, benzenesulfonic, 4-methylbenzenesulfonic, 2-methylbenzenesulfonic, methanesulfonic, citric, phosphoric, trifluoroacetic, 4-nitrobenzene sulfonic, tetrafluoroboric, hexafluorophosphoric or other acid, and subsequent obtaining 2,2-dimethyl-6-((4-((3,4,5-trimethoxyphenyl)amino)-1,3,5-triazine-2-yl) amino)-2H-pyrido[3,2-b][1,4]oxazine-3(4H)-one base from this salt and repeated synthesis of the salt with 4-methylbenzenesulfonic acid from this base.

A free base 2,2-dimethyl-6-((4-((3,4,5-trimethoxyphenyl) amino)-1,3,5-triazine-2-yl)amino)-2H-pyrido[3,2-b][1,4] oxazine-3(4H)-one is known and described in patent No. RU2509770.

DETAILED DISCLOSURE OF INVENTION

As the result of conducted studies it was found that 2,2-dimethyl-6-((4-((3,4,5-trimethoxyphenyl)amino)-1,3,5-triazine-2-yl)amino)-2H-pyrido[3,2-b][1,4]oxazine-3(4H)-one (hereinafter referred to as the Compound 1) has a modulating activity toward the Src-kinase family, particularly toward human c-Src kinase at half-maximal inhibitory concentration within a nanomolar range. At the same time, it was established that pharmacokinetics of this compound is not acceptable to use the compound in clinical practice as a drug for treating the diseases related to aberrant kinase activity, which leads to aberrant bone and cartilage metabolism. Specifically, studies of Compound 1 pharmacokinetics at oral administration in rats at a dose of 30 mg/kg showed maximum concentration in the animal blood plasma 100 times lower than the minimum effective concentration established in studies of efficacy (see details in Examples section).

This problem, as it is described in this invention, is solved by development and preparation of a new salt form being a salt of 4-methylbenzenesulfonic acid and Compound 1 as a base.

It was found, that the salt of 4-methylbenzenesulfonic acid and Compound 1 is mostly effective in c-Src kinase activity inhibition ($IC_{50}$=14 nmol/l). Furthermore, we found an apparent inhibitory effect of this Compound 1 salt form on bone tissue catabolism. The specified effect is related to inhibition of osteoclast-mediated resorption of bone tissue, which was demonstrated by in vitro experiments in a model system using mature human osteoclasts. Compounds according to the invention are promising for treating musculoskeletal diseases related to aberrant bone metabolism, particularly for treating diseases resistant to other treatment methods. Examples of such diseases include osteoporosis, particularly secondary osteoporosis and especially secondary osteoporosis at rheumatoid arthritis. Besides, the salt of 4-methylbenzenesulfonic acid and Compound 1 as well as its hydrate (monohydrate in particular) and/or polymorphic modifications can be used for treatment of diseases related to decrease in bone mineral mass and density, deterioration of bone quality due to deterioration of bone microarchitecture, microdamage accumulation, disorders of bone mineralization and bone remodeling rate.

In the course of the study it was unexpectedly established, that the salt of 4-methylbenzenesulfonic acid and Compound 1, as well as its solvate, hydrate (monohydrate in particular) and polymorphic modifications have suitable pharmacokinetics and can be used for treatment of diseases featured by aberrant bone and cartilage metabolism. It was unexpectedly found that single administration of the salt of 4-methylbenzenesulfonic acid and Compound 1 requires significantly lower dose to achieve the required therapeutic effect as compared with other salt forms of the Compound 1.

The in vivo experiment also showed that 4-methylbenzenesulfonic acid and Compound 1 salt hydrate has a linear pharmacokinetics within a wide range of doses at intragastric administration of the drug in Wistar rats. Daily average concentration of the Compound 1 in target organs (bone and cartilage tissues) exceeds daily average concentration of Compound 1 in animal blood plasma more than three times.

Besides, a study of biological activity of the Compound 1 salt form according to the invention allowed to establish an apparent dose-related positive effect on IL-18-induced hypertrophic changes in chondrocytes associated with aberrant cartilage metabolism, which is characteristic for osteoarthritis and manifest as significant increase of aggrecan expression. This effect leads to cartilage anabolism acceleration related to more than four-time increase of aggrecan production while aggrecan is one of the cartilage components.

Thus, using a Src-family kinase inhibitor, particularly c-Src kinase inhibitor, according to the invention as a drug for a single-drug therapy or in combination with other methods for musculoskeletal diseases treatment allows achieving a significant and prolonged remission. The c-Src kinase inhibitor according to the invention can be used as a supportive treatment agent serving to prevent possible relapses in patients who need such treatment.

DESCRIPTION OF FIGURES

FIG. 1. Crystallization of Compound 1 salts, 100 mg.

FIG. 2. Crystallization of Compound 1 salts, 2,000 mg.

FIG. 3. Results of Compound 1 salt form elemental analysis. Calculated values for monohydrates of correspondent salts are given in parenthesis.

FIG. 4. X-ray diffraction patterns of hydrochloric acid and Compound 1 salt powder: a) S-3-10-B-HCl sample; b) S-3-11-C2-HCl sample.

FIG. 9. X-ray diffraction patterns of 4-methylbenzenesulfonic acid and Compound 1 salt monohydrate:
a) S-3-12-A1-TSA sample, polymorphic modification A;
b) SYK 91/1 sample, polymorphic modification B.

FIG. 11. General view of an independent part of a unit cell of 4-methylbenzenesulfonic acid and Compound 1 salt hydrate:
a) S-3-12-A1-TSA sample, polymorphic modification A;
b) SYK 91/1 sample, polymorphic modification B.

b)$^{13}$C NMR spectrum (Bruker DRX500, 125.76 MHz, DMSO-d6).

Figure 14:
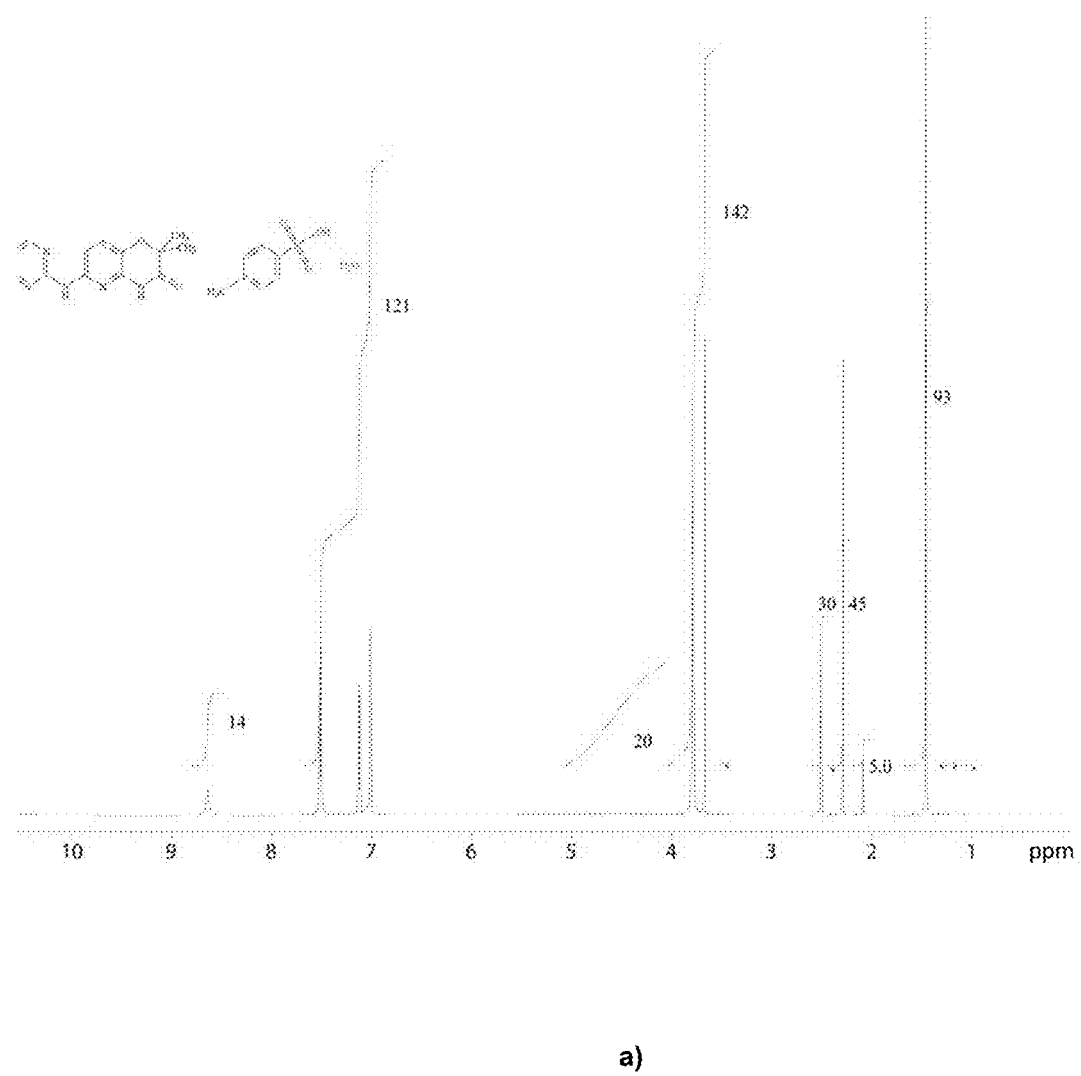
Figure 14:
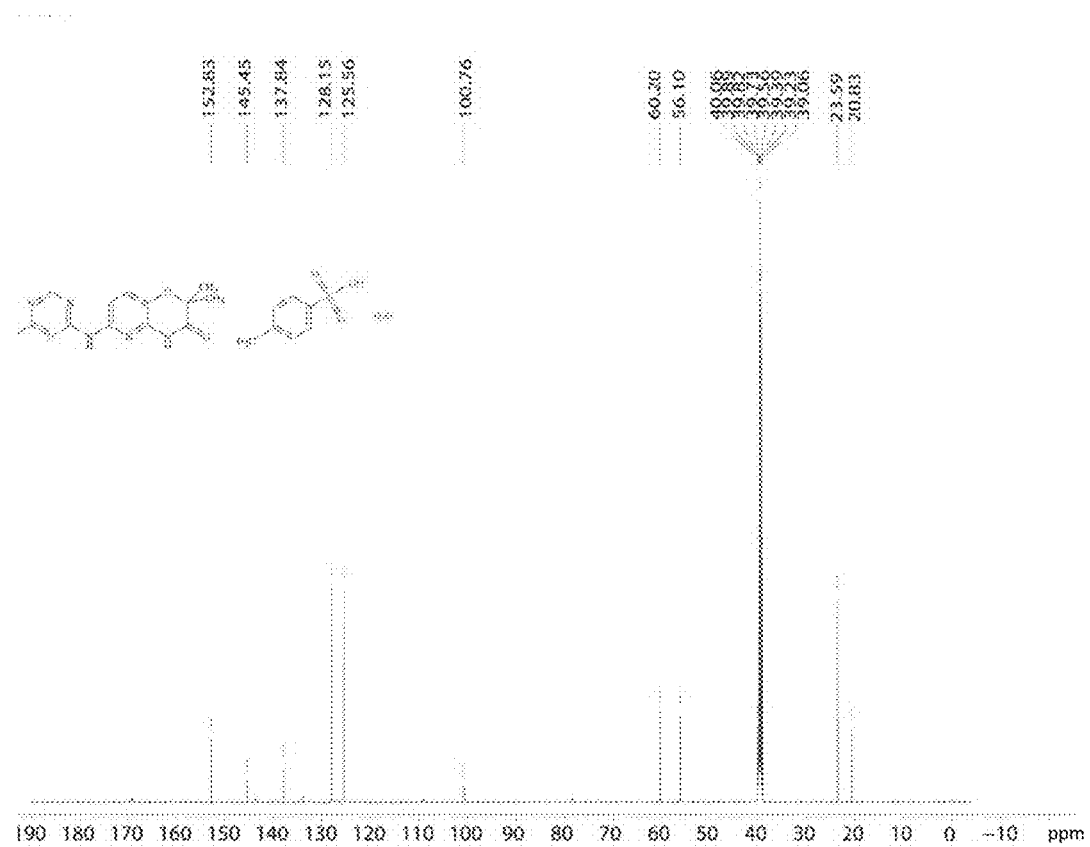

FIG. 14. $^{1}$H Vl $^{13}$C NMR spectra of salt hydrate of 4-methylbenzenesulfonic acid and Compound 1 (polymorphic modification B):
a)$^{1}$H NMR spectrum (Bruker DRX500, 13, 500.13 MHz, DMSO-d6);
b)$^{13}$C NMR spectrum (Bruker DRX500, 13, 125.76 MHz, DMSO-d6).

Figure 15:
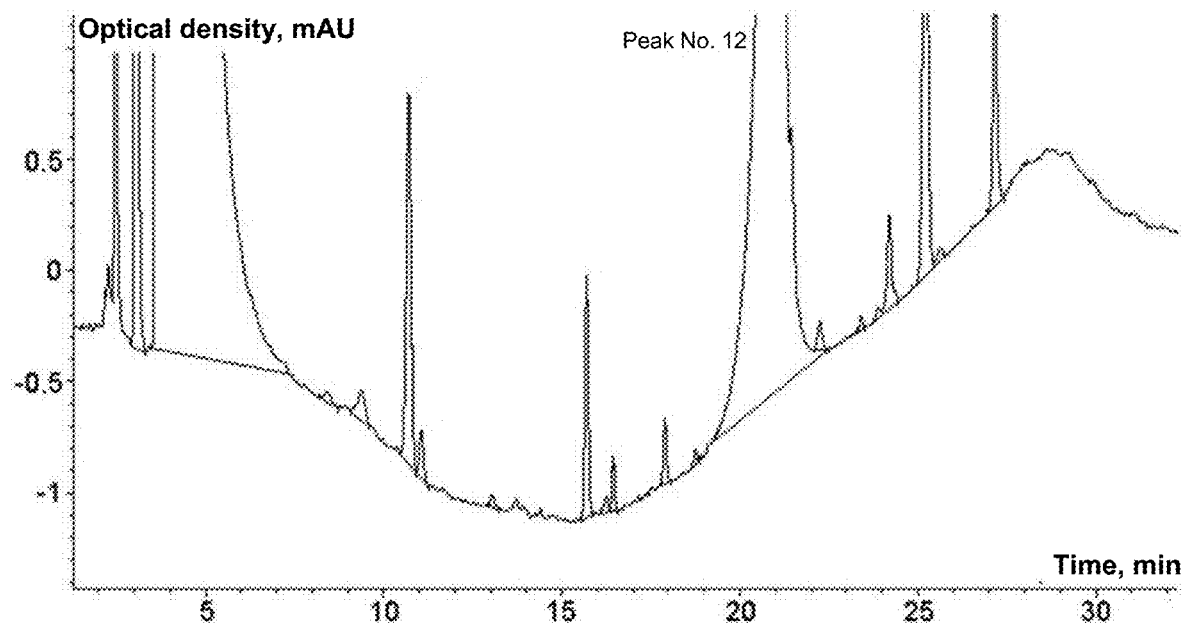

FIG. 15. HPLC curves of Compound 1 free base sample.

Figure 16:
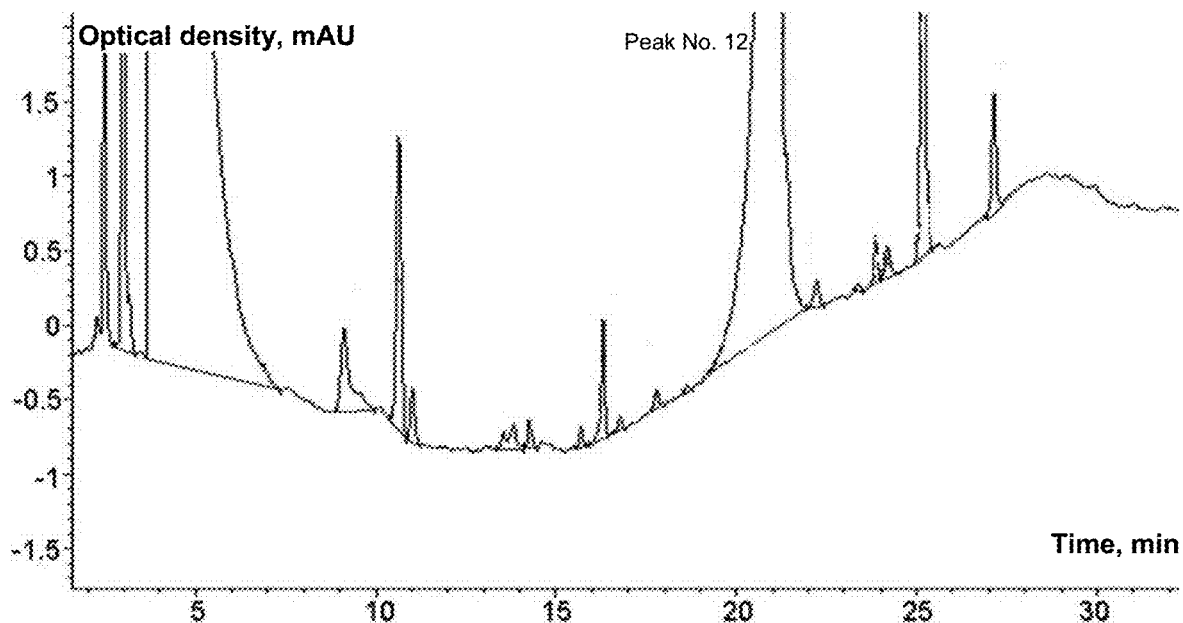

FIG. 16. HPLC curves of methanesulfonic acid and Compound 1 salt sample.

FIG. 17. HPLC curves of 4-methylbenzene sulfonic acid and Compound 1 salt hydrate samples:
a) polymorphic modification A;
b) polymorphic modification B.

Figure 18:
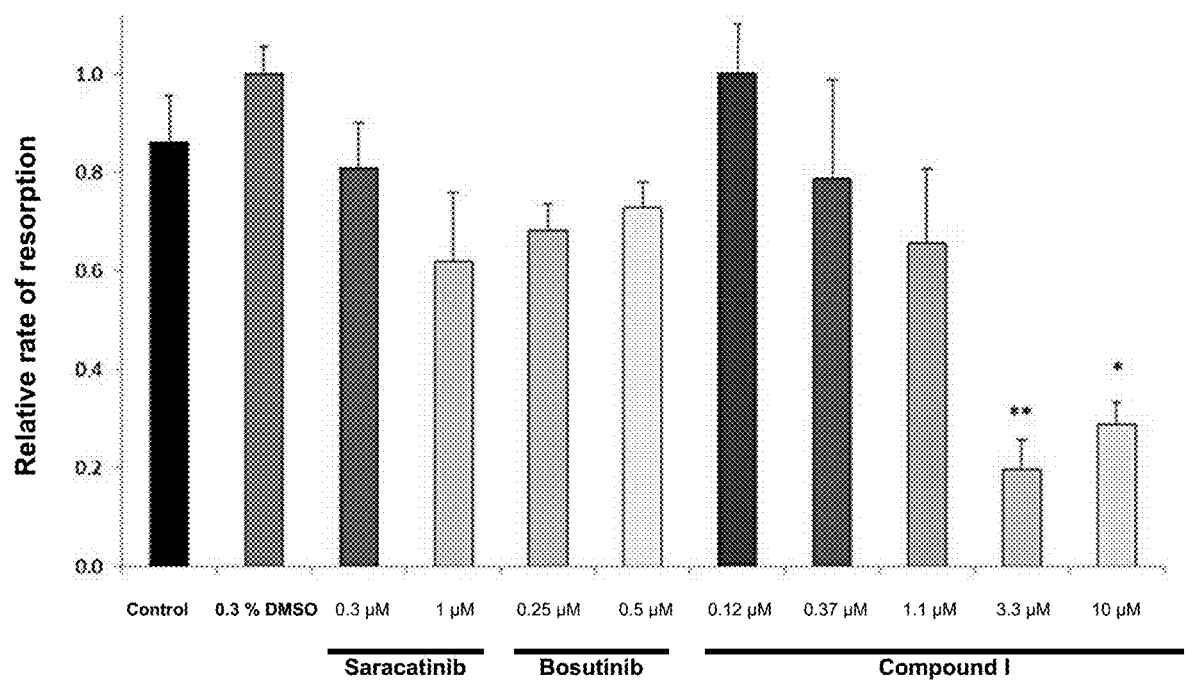

FIG. 18. Influence of saracatinib, bosutinib and Compound 1 on relative resorption of a mineralized matrix.

Figure 19:
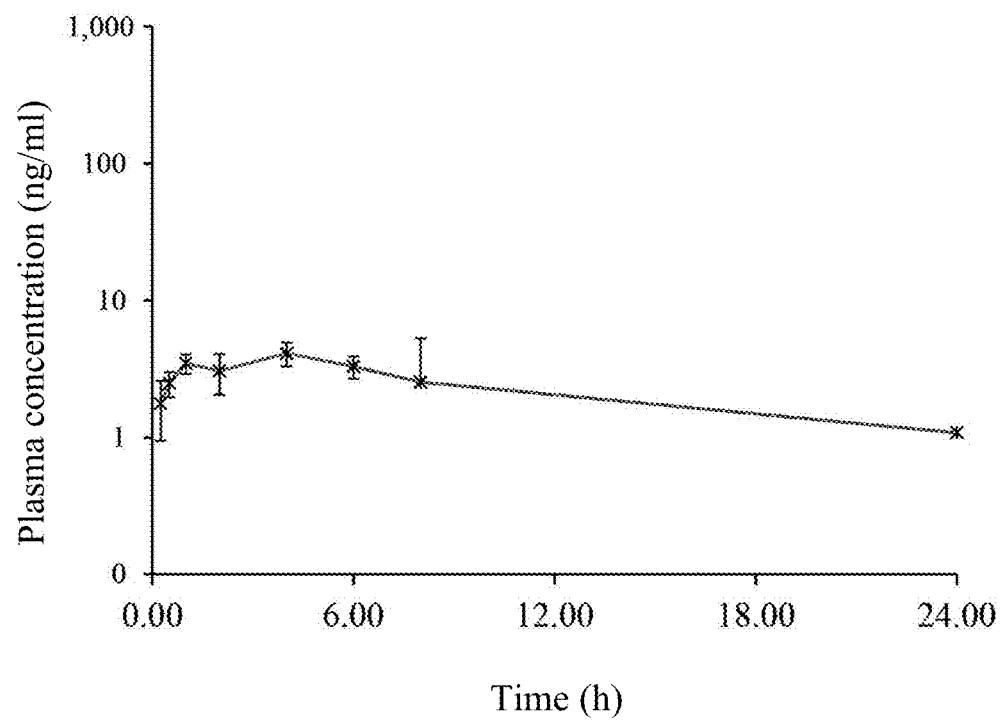

FIG. 19. Average concentrations of the Compound 1 in Wistar rat blood plasma after a single oral administration of a free base at a dose of 30 mg/kg. Average values for each time point are determined based on individual data received in three animals.

Figure 20:
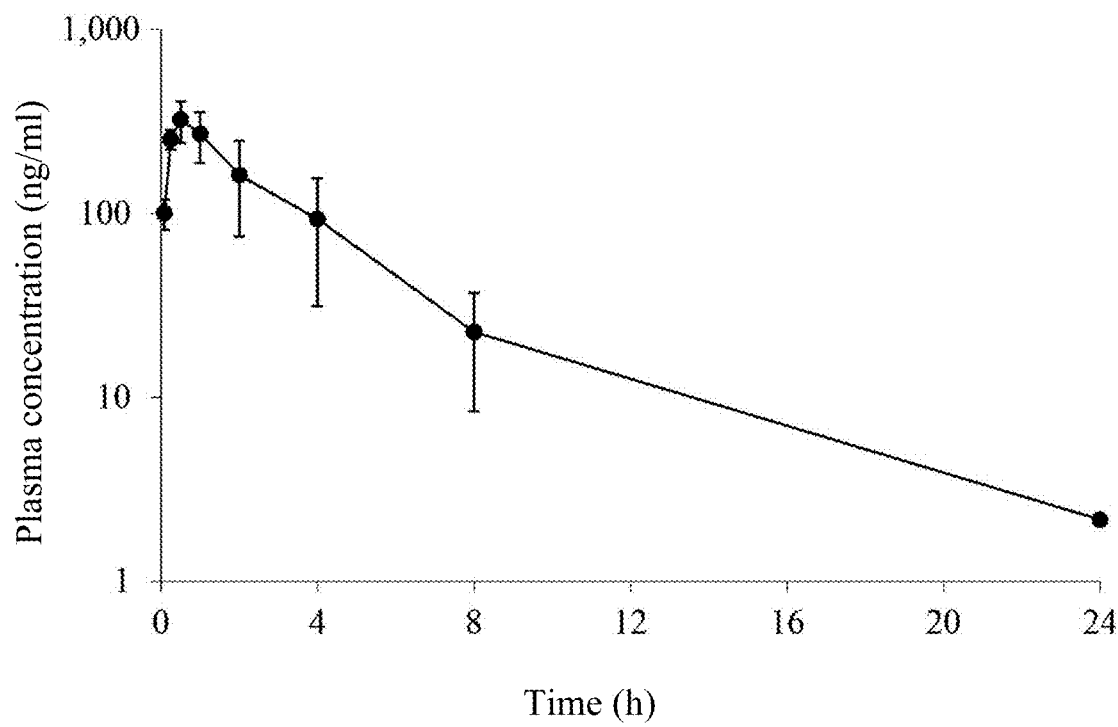

FIG. 20. Average concentrations of the Compound 1 in Wistar rat blood plasma after a single oral administration of Compound 1 mesylate at a dose of 30 mg/kg (free base equivalent). Average values for each time point are determined based on individual data received in three animals.

Figure 21:
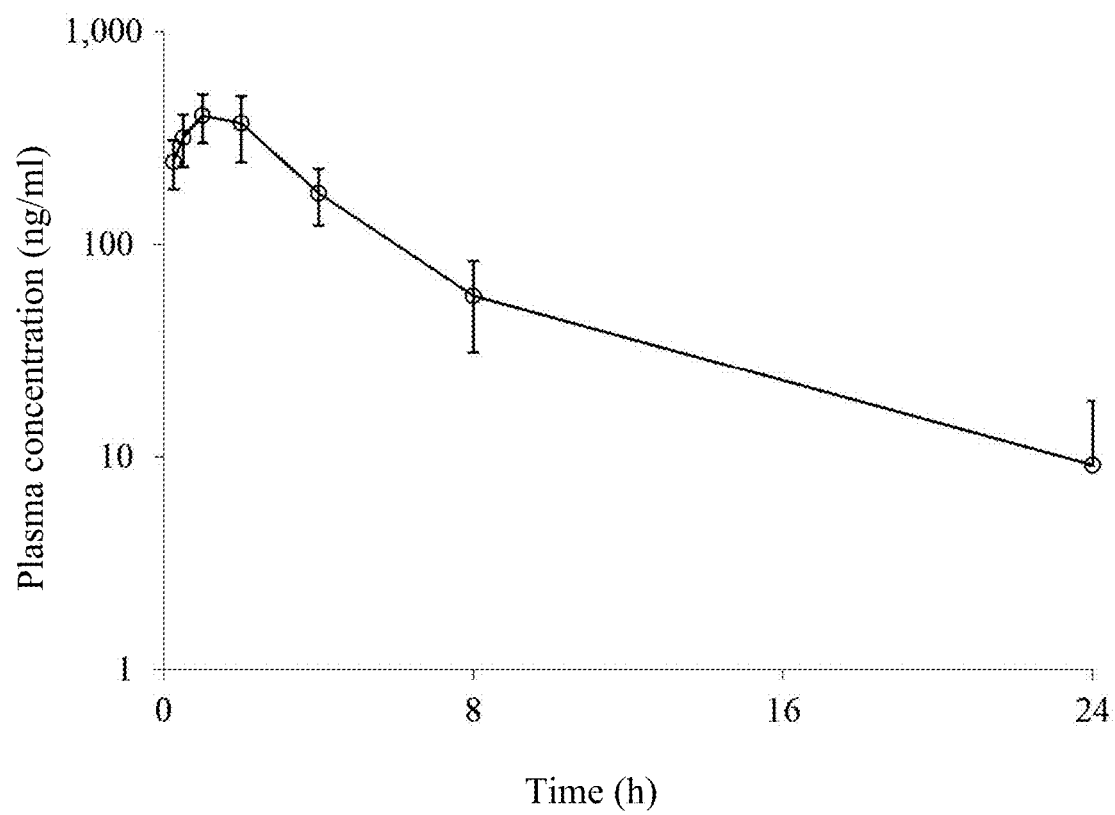

FIG. 21. Average concentrations of the Compound 1 in Wistar rat blood plasma after a single oral administration of 4-methylbenzenesulfonic acid and Compound 1 salt hydrate (polymorphic modification A) at a dose of 21 mg/kg (free base equivalent). Average values for each time point are determined based on individual data received in six animals.

TERMS AND DEFINITIONS

For the purposes of this document, the term Compound 1 refers to 2,2-dimethyl-6-((4-((3,4,5-trimethoxyphenyl)amino)-1,3,5-triazine-2-yl)amino)-2H-pyrido[3,2-b][1,4]oxazine-3(4H)-one, which is also presented as a structural formula:

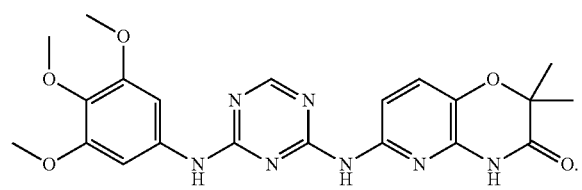

The term C, when used with reference to temperature, means a centigrade scale or a Celsius temperature scale.

The term $IC_{50}$ means concentration of a tested compound at which half-maximal inhibition of kinase activity is achieved.

The term suspension refers to a solid substance suspended in a liquid media, usually in water or an organic solvent.

The term modulation in this document refers to modification of kinase catalytic activity. Particularly, the modulation refers to activation or inhibition of the kinase catalytic activity. The term polymorphic modification refers to a solid substance phase which can have several different forms due to various position and/or conformation of molecules in a crystal structure. The polymorphic modifications usually have different chemical and physical properties. Besides, the term polymorphic modification also refers to solvates, hydrates (i.e., crystalline forms containing a solvent or water), as well as to various non-solvated and non-hydrated crystalline forms of a compound.

The term solvate is used to describe a molecular complex containing a compound according to the invention and one or more molecules of a pharmaceutically acceptable solvent, e.g., ethanol. The term hydrate is used if water is used as the solvent.

The term powder X-ray diffraction pattern or PXRD pattern refers to an experimentally observed diffraction pattern or to data obtained therefrom. Generally the powder X-ray diffraction patterns are characterized by a position (at the x-axis) and intensity (at the y-axis) of a peak. The term peak intensity refers to a relative intensity of a signal at a particular X-ray diffraction pattern. Factors influencing on the relative peak intensity are sample thickness and preferable orientation (i.e., distribution of crystalline particles is not accidental). The term peak position, for the purposes of this application, refers to position of an X-ray reflection position measured and observed in powder diffraction experiments. Peak positions are directly related to sizes of a unit cell. Peaks identified by their correspondent position are obtained based on the diffraction pattern for different polymorphic forms of 2,2-dimethyl-6-((4-((3,4,5-trimethoxyphenyl)amino)-1,3,5-triazine-2-yl)amino)-2H-pyrido[3,2-b][1,4]oxazine-3(4H)-one salts.

The term 2-teta value or 2θ refers to a peak position in degrees based on the experimental data of the X-ray diffraction. Generally this is a measurement unit at x-axis of diffraction patterns. θ is an angle at which the diffraction conditions for a particular wave length are met. An angle between the diffracted beam direction and initial beam makes 2θ. It should be understood that in this application the reference to specific values of 2θ for a specific polymorphic form implies value of 2θ in degrees measured using experimental conditions of the X-ray diffraction disclosed in this application.

The term aberrant activity of kinase in this document means kinase activity which is significantly different from a basic level of the kinase activity in cells when no pathology present.

The aberrant activity can arise from changes of kinase expression level, abnormality of processes resulting in kinase activation, deregulation of degradation pathways as well as from other factors.

The term auxiliary substance means any pharmaceutically acceptable substance of non-organic or organic nature included in a composition of a drug or used in the process of the drug production to impart required physical and chemical properties thereto.

The term AUC (area under the curve) means a pharmacokinetic parameter characterizing total concentration of the drug in blood plasma within the entire observation period. It is mathematically determined as an integral 0 to °° of function (pharmacokinetic curve) of drug concentration in blood plasma to time and it is equal to figure area formed by the pharmacokinetic curve and axes of coordinates.

Src-kinase family is a family on non-receptor tyrosine-protein kinases of mammals having a structure similar to the one of c-Src kinase. In vertebrates, nine kinases of the Src family are known: Src, Yes, Fgr, Fyn. Lyn, Fick, Lck, Blk, Frk. Kinases of this family are involved in cell growth regulation, intracellular signaling and particularly in signaling pathways of T- and B-cell receptors, adhesive interactions between cells, etc. The Src-family kinases take an active role in processes related to bone and cartilage metabolism as well as in progress of autoimmune inflammatory processes. c-Src kinase plays key role in formation of an actin ring, which is a unique osteoclast cytoskeleton required for bone resorption.

Syk-kinase (Spleen tyrosine kinase) is a non-receptor cytoplasmic tyrosine kinase involved in transfer of signals by antigen and Fc receptors, BCR and other receptors. The most intensive Syk kinase expression takes place in haematopoietic cells (such as macrophages, mast cells, white blood cells, platelets, and red blood cells); the expression is less intensive in epithelial cells, fibroblasts, neuronal cells, hepatocytes, etc. (Yanagi, S., et al., Biochem BiophysRes Commun, 2001, 288, 495-8). Syk kinase takes part in acquired immunity development and plays an important role in a function of supplementary type cells including platelets, phagocytes, fibroblasts and osteoclasts. Syk kinase plays role in differentiation and functioning of osteoclasts. Besides, Syk kinase plays a particular role in osteolysis process.

The terms treatment, therapy cover management of pathological conditions in mammals, preferably in human, and include: a) mitigation; b) blocking (arrest) of disease progression; c) alleviation of disease severity, i.e., inducing disease regression; d) reversing a disease or condition to which the term is applied to, or one or more symptoms of this disease or condition.

The terms prophylaxis, prevention covers elimination of risk factors as well as preventive treatment of subclinical stages of a disease in mammals, preferably in human, aimed at reducing probability of clinical stage disease development. Patients for the prevention treatment are selected in comparison with general population based on factors which are known to lead to increase in risk of clinical stage disease onset. The preventive treatment includes a) primary prophylaxis and b) secondary prophylaxis. The primary prophylaxis is defined as preventive treatment of patients whose disease has not progressed to the clinical stage yet. The secondary prophylaxis means prevention of relapse or similar clinical state of the disease.

The compounds of this invention are promising for treatment of musculoskeletal diseases related to disorder of bone and/or cartilage metabolism and dystrophic degeneration processes in these tissues, particularly of osteoporosis, osteoarthritis (deforming arthrosis) and osteochondrosis of any etiology and of any systemic or local nature including those conditioned by primary pathological changes in these tissues or related to various diseases or long-term administration of some drugs. In some particular embodiments, the compounds according to the invention can be used for treatment of postmenopausal osteoporosis, senile osteoporosis, drug-induced osteoporosis, osteoporosis in patients with cancer, secondary osteoporosis at rheumatoid arthritis, gonarthrosis, coxarthrosis, osteochondrosis of lumbar, thoracic and cervical spine areas, etc.

Salt Form

Search for a suitable salt for the appropriate drug is critical for a preclinical phase of drug studies. Modification of an active ingredient salt form is commonly used for modification of its chemical and biological properties not leading to its structure modification. Selection of a particular salt form can have significant effect on physical and chemical properties of the drug (e. g., dissolution rate, solubility, stability and hygroscopicity). Replacing one salt form in the drug for another can change therapeutic efficacy, safety and/or quality, which are the most important for a dosage form optimal composition for large-scale production. However, there is no a reliable method to exactly predict an effect of changes in active ingredient salt form on the drug biological activity. Furthermore even after preparation of many salts of the same basic agent, no effective screening techniques exist to facilitate selection of the salt most likely to exhibit the desired pharmacokinetics, solubility and formulation profiles. Briefly speaking, there is no a reliable way of predicting influence of particular salt types on behavior of a basic compound in dosage forms (Berge et al., Pharmaceutical Salts//Journal Pharm. Sci., 1977, Vol. 66, No. 1; Verbeeck et al. Generic substitution: The use of medicinal products containing different salts and implications for safety and efficacy//EP Journal Pharm. Sci, 28, 2006, 1-6).

Solid salt forms are usually preferred for oral administration since they are likely to exhibit required physical properties; and in case of basic drug, acid addition salts are often a preferable salt form. As already mentioned above, different salt forms widely vary in terms of their capability to impart the required properties (such as stability at storage, ease of production and purification processes, pharmacokinetic parameters), and these properties can not be predicted accurately enough. E. g., some salts are solids at ambient temperature, while other salts are liquids, thick oils or resins. Besides, some salt forms are stable at stress heat and light exposure while others are readily decomposed even at mild conditions. Therefore, the development of an appropriate form of acid added salt of basic agent for use in a pharmaceutical composition is a critical and not always predictable process.

Pharmacokinetic parameters are the most important properties determining suitability of a solid salt form (or particular polymorphic modification) for use as a drug. Average daily and maximum concentrations of a drug in animal and human blood can significantly depend on a salt form content and polymorphic modification. Possibility of large-scale production of the selected salt form of a drug substance and purity (or purification complexity) of a produced product are critical characteristics essentially dependent on the selected salt form. Furthermore, since the pharmaceutical compositions containing drug substances shall have an adequate storage period, the suitable salt forms shall not exhibit significant changes in physical and chemical properties (chemical composition, water content, density, hygroscopicity, solubility, etc.) when stored for a prolonged period of time.

The solid substances including pharmaceutically active compounds often have more than one crystalline form; this property is known as polymorphism. The polymorphism often takes place when a compound is crystallized into multiple different solid phases which vary in terms of crystal packing. The polymorphic modifications (polymorphs) usually have different physical properties including solubility, physical and chemical stability. Various solid salt forms of the same drug substance, moreover, various polymorphs of the same solid salt form can differ in a rate of drug release, solid stage stability of the salt form and suitability for pharmaceutical production.

Therefore, to produce commercially feasible and pharmaceutically acceptable medicinal compositions, it is important to offer (when possible) a drug in essentially stable crystalline forms (or form).

Method of Therapeutic Use of the Compounds

The object of this invention also includes administration of a therapeutically effective amount of the compound according to the invention to a subject in need of the correspondent treatment. The therapeutically effective amount means such amount of the compound introduced or administered to a patient, at which the desired response to treatment (prophylaxis) is most likely in the patient. An exact required amount can vary for various patients depending on age, body weight and general state, disease severity, drug administration route, combination with other drugs, etc.

The compound according to the invention or a pharmaceutical composition containing the compound can be introduced in the patient's body in any amount (preferably a daily dose of the active ingredient makes up to 1.5 g per a patient a day; mostly preferable, a daily dose makes 200 to 500 mg a day) and by any administration route (preferably orally), which is effective in treatment or prophylaxis.

When the drug is mixed with a particular appropriate and pharmaceutically accepted carrier at a desired proportion, the compositions being the invention essence can be introduced in a body of a human or animals orally, parenterally, locally, etc.

The drug can be administered both as a single dose and several times a day, a week (or any other time interval) or from time to time. Besides, the compound can be introduced into the patient's body daily during a particular period (e. g., 2 to 10 days) followed by a period without administration (e. g., 1 to 30 days).

In case when the compound according to the invention is used as a part of a combined therapy regimen, dose of each component of the combined therapy is administered during the required period of treatment. The compounds comprising the combined therapy can be introduced into the patient's body both at the same time as a dosage form containing all the components, and as individual dosage forms of components.

Pharmaceutical Compositions

The invention also covers pharmaceutical compositions containing the compounds according to the invention (or a prodrug form or other pharmaceutically acceptable derivative) and one or more pharmaceutically acceptable carriers, adjuvants, solvents and/or excipients which can be introduced into the patient's body together with the compound being the essence of this invention, and which do not impair pharmacological activity of this compound and have no toxic effects when administered at dosages sufficient to deliver the therapeutic amount of the compound.

The pharmaceutical compositions declared in this invention contain combination of this invention with pharmaceutically acceptable carries, which can include any solvents, diluents, dispersions or suspensions, surfactants, isotonic agents, gelifiers, emulsifiers, preserving agents, binding agents, lubricants, etc., suitable for a particular dosage form. Materials suitable to be the pharmaceutically acceptable carriers include but not limited to mono- and oligosaccharides as well as derivatives thereof; gelatine; talc; excipients such as cocoa oil and wax for suppositories; oils such as peanut, cottonseed, safrole, sesame, olive, corn and soybean oils; glycols such as propylene glycol; esters such as ethyl oleate and ethyl laurate; agar; buffering agents such as sodium hydroxide and aluminum hydroxide; alginic acid; pyrogen-free water; isotonic solution; Ringer's solution; ethyl alcohol and phosphate-buffer solutions. The composition can also contain other non-toxic compatible lubricants such as sodium lauryl sulfate and magnesium stearate as well as coloring agents, parting fluids, film-forming materials, sweeteners, flavoring agents, preserving agents and antioxidants.

This invention also covers dosage forms, i.e., a class of pharmaceutical compositions which content is optimized for a particular route of introducing into a body at a therapeutically effective dose, e. g., orally, locally, by pulmonary route, e. g., by inhalation spray or intravenously, by intranasal route, subcutaneous route, intramuscularly as well as by infusion at recommended doses.

The dosage forms of this invention can have a content obtained by using liposomes, microcapsulation, nanoform preparation and other methods known in the field of pharmaceutics.

When a composition has a form of a tablet, for instance, the active ingredient is mixed with one or several pharmaceutical excipients such as gelatine, starch, lactose, magnesium stearate, talc, silica, acacia, mannitol, microcrystalline cellulose, hypromellose or similar compounds.

The tablets can be coated with sucrose, cellulose derivative or other substances suitable for coating. The tablets can be obtained by various methods such as direct pressing, dry or wet granulation or hot-melting.

A pharmaceutical composition in a form of gelatine capsule can be obtained by mixing the active ingredient with a solution and filling soft or hard capsule with an obtained mixture.

To administer a drug parenterally, various water suspensions, isotonic salines or sterile injection solutions containing pharmacologically compatible agents, e. g., propylene glycol or butylene glycol, are used.

Examples of Pharmaceutical Compositions

The substances described in the present invention can be used for prophylaxis and/or treatment of human or animal diseases in a form with composition presented below (the Substance means an active ingredient):

| Tablet I | mg/tablet |
| --- | --- |
| Substance | 50 |
| Lactose Ph. Eur | 223.75 |
| Croscarmellose sodium | 6.0 |
| Corn starch | 15 |
| Polyvinylpyrrolidone (5% w/v paste) | 2.25 |
| Magnesium stearate | 3.0 |

| Tablet II | mg/tablet |
| --- | --- |
| Substance | 200 |
| Lactose Ph. Eur | 182.75 |
| Croscarmellose sodium | 12.0 |
| Corn starch (5% w/v paste) | 2.25 |
| Magnesium stearate | 3.0 |

| Capsule | mg/capsule |
| --- | --- |
| Substance | 10 |
| Lactose Ph. Eur | 488.5 |
| Magnesium Sulfate | 1.5 |

| Injection composition I | (50 mg/ml) |
| --- | --- |
| Substance | 5.0% w/v |
| 1M sodium hydroxide solution | 15.0% w/v |
| 1M hydrochloric acid solution | ad pH 7.6 |
| Polyethylene Glycol 400 | 4.5% w/v |
| Water for injection | ad 100% |

| Ointment | ml |
| --- | --- |
| Substance | 40 mg |
| Ethanol | 300 μl |
| Water | 300 μl |
| 1-dodecylazacycloheptanone | 50 μl |
| Propylene glycol | ad 1 ml |

These compositions can be prepared in compliance with the standard pharmaceutical techniques. The tablets (I)-(II) can have an enteric coating, e. g., using cellulose acetate phthalate.

EXAMPLES

Obtaining the Compounds According to the Invention

Synthesis of 2,2-dimethyl-6-((4-((3,4,5-trimethoxyphenyl)amino)-1,3,5-triazine-2-yl)amino)-2H-pyrido[3,2-b][1,4]oxazine-3(4H)-one (Compound 1)

193.2 g (1 mol) of 6-amino-2,2-dimethyl-2H-pyrido[3,2-b][1,4]oxazine-3(4H)-one is added in portions to 165 g solution (1.1 mol) of 2,4-dichlortriazine and 98.5 g (1.2 mol) of anhydrous sodium acetate in 2,000 ml of glacial acetic acid within 30 minutes while agitating and maintaining temperature not exceeding 30° C. The reaction mixture is left to stand overnight, precipitate is filtered, rinsed on the filter by acetic acid (2×500 ml), by water ad neutral reaction and dried. 220 g of 6-((4-chloro-1,3,5-triazine-2-yl)amino)-2,2-dimethyl-2H-pyrido[3,2-b][1,4]oxazine-3(4H)-one are obtained.

306.7 g (1 mol) of 6-((4-chloro-1,3,5-triazine-2-yl)amino)-2,2-dimethyl-2H-pyrido[3,2-b][1,4]oxazine-3(4H)-one and 384.7 g (2.1 mol) of 3,4,5-trimethoxyaniline are added to 3 l of degassed ethylene glycol while intensively agitating. After that, the reaction mixture is heated up to 110° C. and is being agitated at this temperature for 4 hours. After 4 hours the reaction mixture temperature is raised to 125° C., the agitation is continued for 4 hours. Then the reaction mixture is cooled to 60° C., precipitate is filtered, rinsed by ethylene glycol (2×500 ml), followed by acetone (3×600 ml) and water (4×1,500 ml), then dried. The output is 365 g of 2,2-dimethyl-6-((4-((3,4,5-trimethoxyphenyl)amino)-1,3,5-triazine-2-yl)amino)-2H-pyrido[3,2-b][1,4]oxazine-3(4H)-one.

Synthesis of salt monohydrate of 4-methylbenzenesulfonic acid and 2,2-dimethyl-6-((4-((3,4,5-trimethoxyphenyl)amino)-1,3,5-triazine-2-yl) amino)-2H-pyrido[3,2-b][1,4]oxazine-3(4H)-one Base (Polymorphic Modification A)

20 g (~0.105 mol) solution of 4-methylbenzenesulfonic acid hydrate in 20 ml ethanol is added as one portion to boiling suspension of 45.3 g (0.1 mol) of 2,2-dimethyl-6-([4-[(3,4,5-trimetoxiphenyl)amino)-1,3,5-triazine-2-yl]amino)-2H-pyrido[3,2-b][1,4]oxazine-3(4H)-one in 1,200 ml of acetone. The mixture is boiled for 30 minutes, then the mixture is slowly cooled to ambient temperature and left to stand overnight. The precipitate is filtered, rinsed on filter with acetone (2×50 ml) followed by diethyl ether (2×100 ml), then dried. Product output is 90%.

$^1$H NMR spectrum (400 MHz, DMSO-d$_6$): 11.13 (s, 1H), 8.57 (s, 1H) 7.52-7.44 (m, 3H) 7.12 (d, 2H, J=8 Hz) 7.02 (s, 2H), 4.4-3.9 (bs, 4H), 3.8 (s, 6H), 3.7 (s, 3H), 2.3 (s, 3H), 1.5 (s, 6H)

Mass spectrum, m/z: 454.18 ([M+nH]$^+$)

Figure 13:
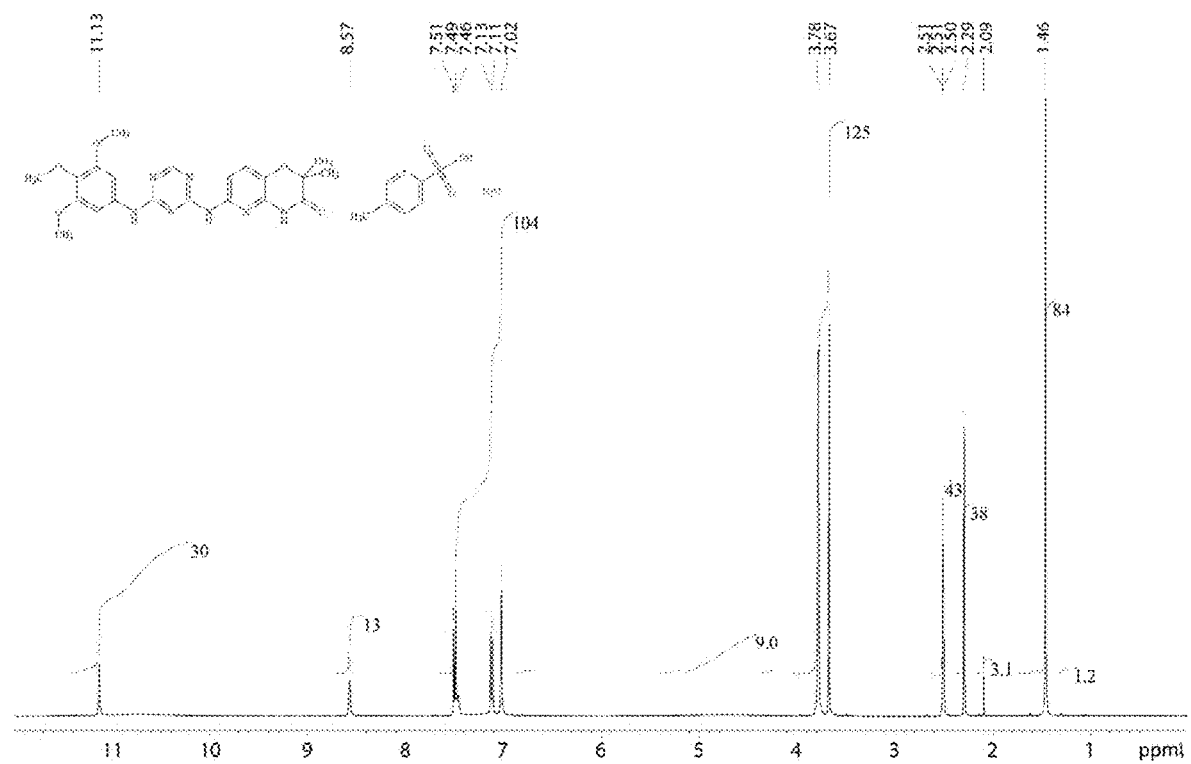
FIG. 13. $^1H$ Vl $^{13}C$ NMR spectra of salt hydrate of 4-methylbenzenesulfonic acid and Compound 1 (polymorphic modification A):
a)$^1H$ NMR spectrum (Bruker DRX500, 13400, 500.13 MHz, DMSO-d6)
Figure 13:
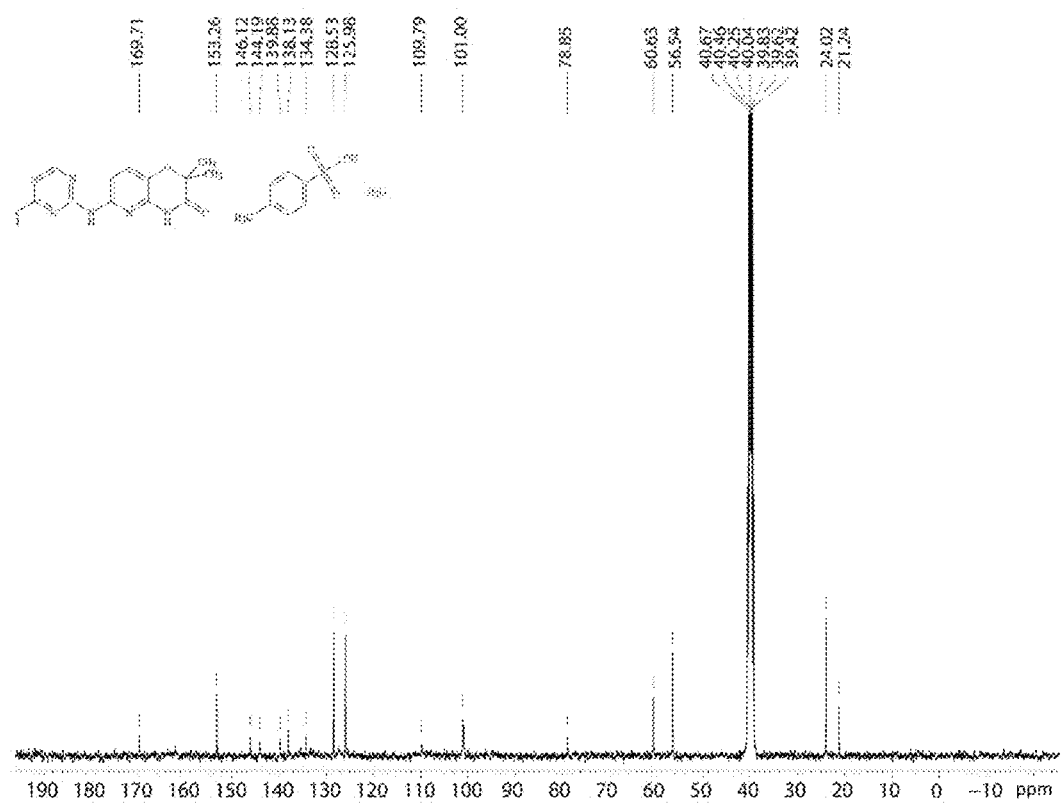

$^1$H and $^{13}$C NMR spectra of salt monohydrate of 4-methylbenzenesulfonic acid and 2,2-dimethyl-6-((4-((3,4,5-trimethoxyphenyl)amino)-1,3,5-triazine-2-yl)amino)-2H-pyrido[3,2-b][1,4]oxazine-3(4H)-one base (polymorphic modification A) are given in FIG. 13.

Synthesis of salt monohydrate of 4-methylbenzenesulfonic acid and 2,2-dimethyl-6-((4-((3,4,5-trimethoxyphenyl)amino)-1,3,5-triazine-2-yl) amino)-2H-pyrido[3,2-1,4]oxazine-3(4H)-one Base (Polymorphic Modification B)

64.4 g (0.1 mol) of 4-methylbenzenesulfonic acid and 2,2-dimethyl-6-((4-((3,4,5-trimetoxphenyl)amino)-1,3,5-triazine-2-yl)amino)-2H-pyrido[3,2-b][1,4]oxazine-3(4H)-one base salt monohydrate (polymorphic modification A) is kept at temperature of 110-115° C. and residual pressure of 6 mbar for 2 hours, then cooled in vacuum. Product output is 100%.

The polymorphic modification B of 4-methylbenzenesulfonic acid and 2,2-dimethyl-6-((4-((3,4,5-trimethoxyphenyl)amino)-1,3,5-triazine-2-yl)amino)-2H-pyrido[3,2-b][1,4]oxazine-3(4H)-one base salt monohydrate can also be obtained by treating the polymorphic modification A with ethanol or other solvent.

$^1$H NMR spectrum (400 MHz, DMSO-de): 11.13 (s, 1H), 8.57 (s, 1H) 7.52-7.44 (m, 3H) 7.12 (d, 2H, J=8 Hz) 7.02 (s, 2H), 4.4-3.9 (bs, 4H), 3.8 (s, 6H), 3.7 (s, 3H), 2.3 (s, 3H), 1.5 (s, 6H)

Mass spectrum, m/z: 454.18 ([M+nH]$^+$).

$^1$H and $^{13}$C NMR spectra of salt monohydrate of 4-methylbenzenesulfonic acid and 2,2-dimethyl-6-((4-((3,4,5-trimethoxyphenyl)amino)-1,3,5-triazine-2-yl)amino)-2H-pyrido[3,2-b][1,4]oxazine-3(4H)-one base (polymorphic modification B) are given in FIG. 14.

Optimization of Compound 1 Salt Form

To obtain a form having optimal biological and physical properties, various salt forms of the Compound 1 was synthesized. A primary goal of the salt form optimization was to obtain a Compound 1 salt form having the following properties: crystallinity, composition stability, therapeutic efficacy, safety, ease of production process scalability, using a pharmacologically acceptable counterion (preferably anion), and using low toxicity organic solvents. The salt forms of Compound 1 were obtained with organic solutions of high polarity and low toxicity (Class 3). The counterions were used based on pharmacological acceptance and high acid strength (pKa not exceeding 3.25). The requirement for the high acid strength is conditioned by the fact that a protonated nitrogen atom of pyridine of the Compound 1 is a weak base having pKa 4.

At the first stage solubility of the primary base in the selected organic solvents was studied. Maximum volume of a solvent for this study was selected as 10 ml per 100 mg of the base taking into consideration the subsequent process scaling. The results of the primary base solubility in the selected organic solvents are given in Table 1.

TABLE 1

The Solubility of the Compound 1 in various solvents

| Code | Amount of base, mg | Solvent | Solvent volume, ml | Temperature, °C | Solubility |
|---|---|---|---|---|---|
| S-1-1-B | 101 | n-Butanol | 10 | 117 | − |
| S-1-2-C2 | 98 | Ethanol | 10 | 78 | − |
| S-1-3-T | 103 | THF | 10 | 66 | − |
| S-1-4-D | 106 | 1,4-Dioxane | 7 | 100 | + |
| S-1-5-A1 | 97 | Acetone | 10 | 56 | − |

At the second stage of the study we attempted to produce salts based on 100 mg of 2,2-dimethyl-6-((4-((3,4,5-trimethoxyphenyl)amino)-1,3,5-triazine-2-yl)amino)-2H-pyrido[3,2-b][1,4]oxazine-3(4H)-one base. For this development stage, pairs of a solvent and an acid were selected in a manner to ensure either complete sample dissolution in the solvent and precipitation after salt adding or homogenization of the system after the acid adding and precipitation after the system cooling to ambient temperature. The results of the Compound 1 salt crystallization study are given in FIG. 1. The following solvent-acid pairs were selected based on the conducted studies: ethanol-HCl, acetone-4-methylbenzenesulfonic acid, as well as n-butanol and dioxane with methanesulfonic acid, camphosulfonic acid, 4-methylbenzenesulfonic acid, HCl, HBr and $H_2SO_4$.

At the third stage, salts in the selected solvent-acid systems were obtained based on 2,000 mg of the base. Scalability of the filtration process was evaluated. The results of these studies are given in FIG. 2. Samples which filtration process was considered as an easily scalable were subjected to an elemental analysis (in order to establish composition stability and stoichiometry) and an analysis by powder X-ray diffraction method (in order to study the structure crystallinity). All the diffraction patterns herein were obtained at 25° C. (±5° C.) and relative air humidity of ≈70% using Bruker D8 Advance powder X-Ray diffraction system in Bragg-Brentano geometry (40 kV anode voltage, 40 mA current), with a nickel filter (CuKα1 radiation, wave length=1.5406 Å) and LynxEye position-sensitive detector, sampling interval=0.02° 2θ, angle range=4 to 65° 2θ. The obtained diffraction patterns were refined using Bruker TOPAS5 software suite.

Based on appropriate scalability of the correspondent salt form production process, we selected solvent-counterion (acid) pairs in which precipitation took place at acid addition or at solution cooling, and the obtained precipitate filtrated easily. These pairs were subjected to the subsequent studies. Thus, the following samples were screened for the following studies: S-3-1-B-TSA (hereinafter S3-1), S-3-2-B-HBr (S3-2), S-3-4-B-HCl (S3-4), S-3-8-B-HBr (S3-8), S-3-9-B-CSA (S3-9), S-3-10-B-HCl (S3-10), S-3-11-C2-HCl (S3-11), S-3-12-A1-TSA (S3-12), S-3-16-D-SA (S3-16) and S-3-17-D-MSA (S3-17).

Samples of these compounds were subjected to an elemental analysis As the result, it was established, that the Compound 1 and 4-methylbenzenesulfonic acid salt samples being monohydrates demonstrate the best reproducibility of the results with the calculated elemental composition (FIG. 3).

Figure 5:
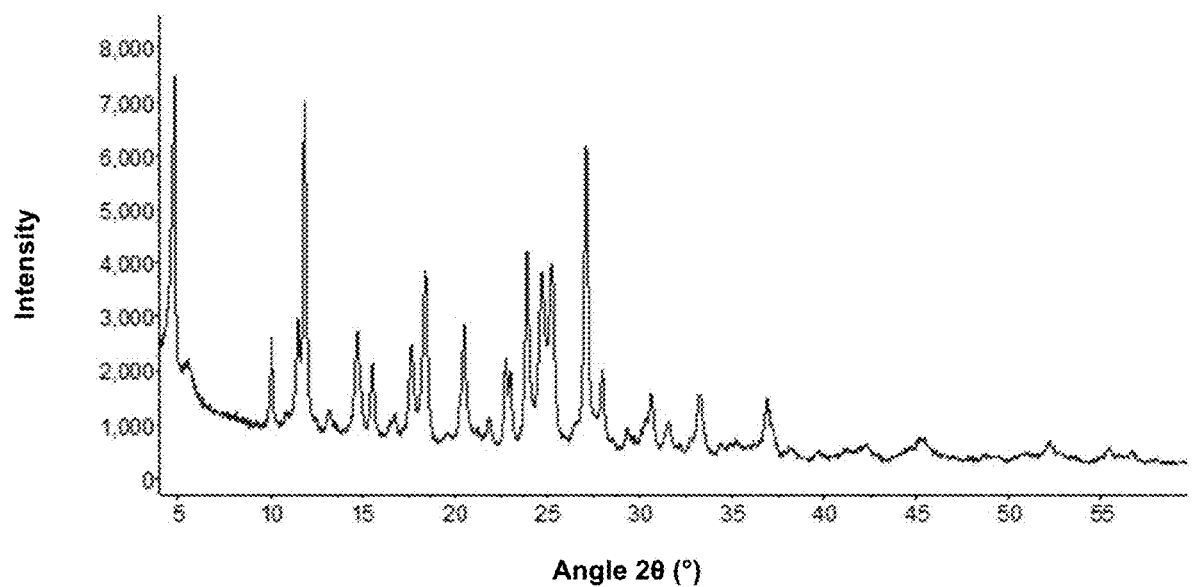
FIG. 5. X-ray diffraction patterns of hydrobromic acid and Compound 1 salt powder (S-3-8-B-HBr sample).
Figure 6:
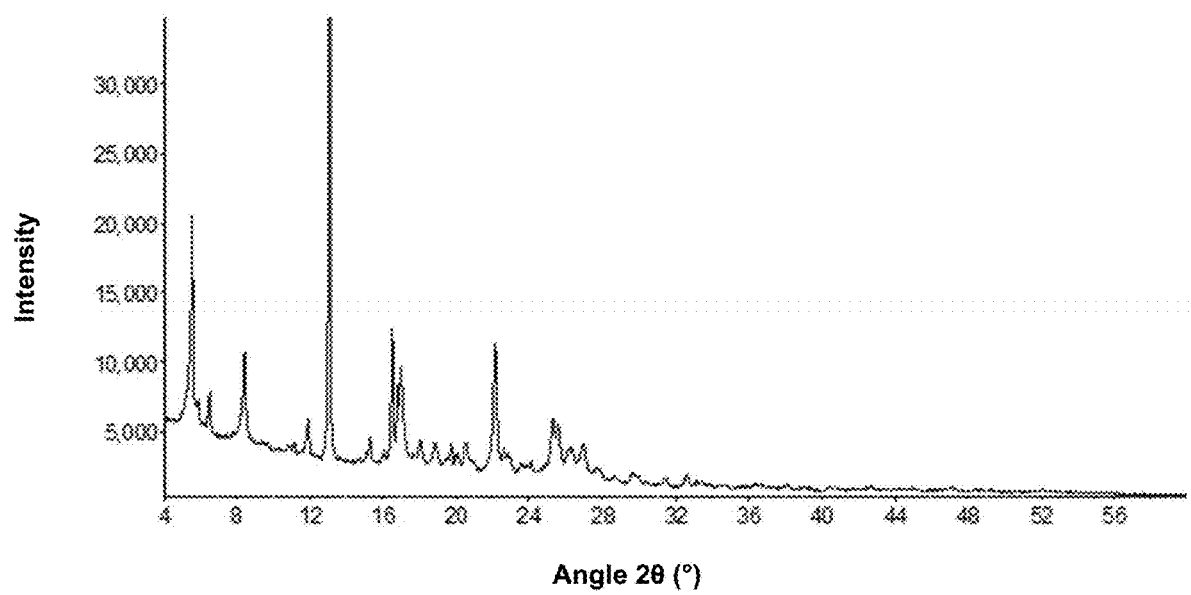
FIG. 6. X-ray diffraction patterns of sulfuric acid and Compound 1 salt powder (S-3-16-D-SA sample).
Figure 7:
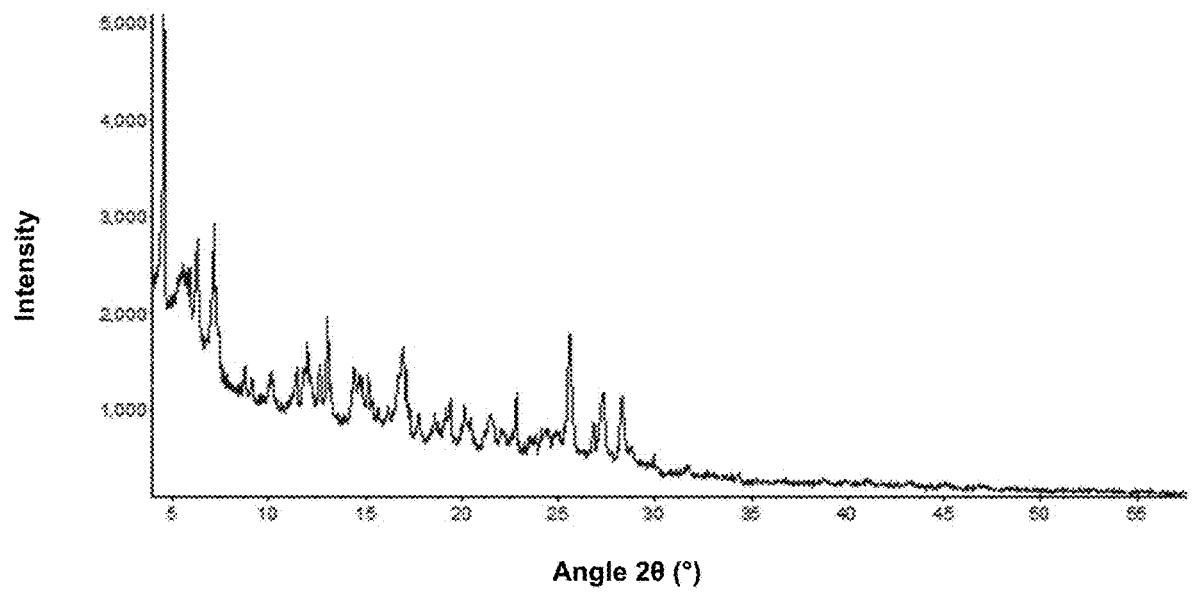
FIG. 7. X-ray diffraction patterns of camphoric acid and Compound 1 salt powder (S-3-9-B-CSA sample).
Figure 8:
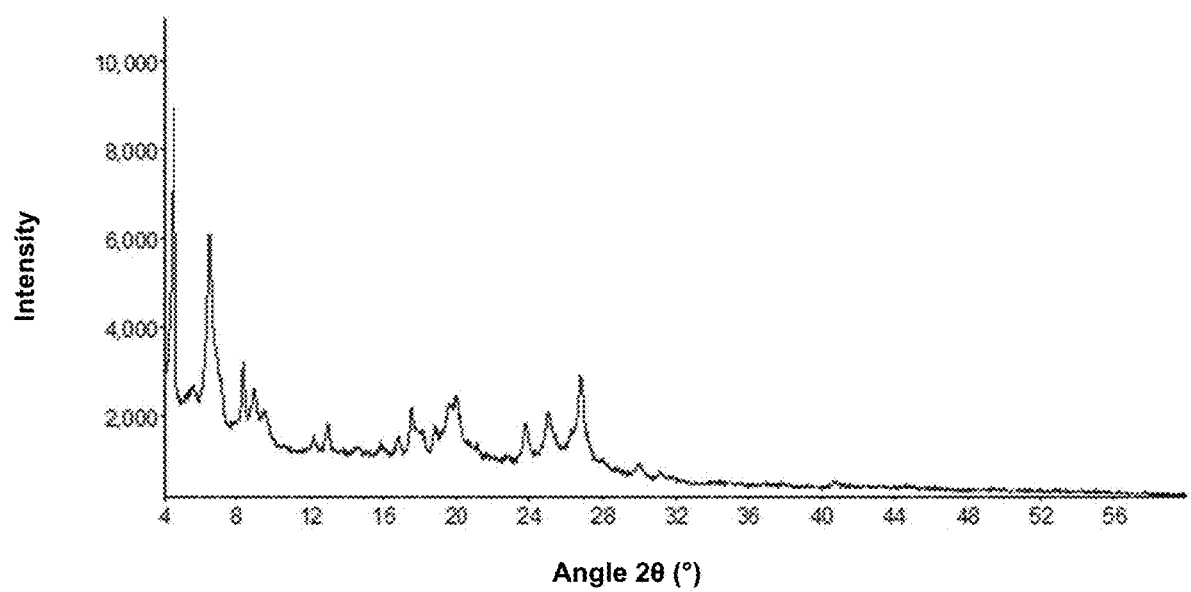
FIG. 8. X-ray diffraction patterns of methanesulfonic acid and Compound 1 salt powder (S-3-17-D-MSA sample).

Further studies of the sample crystallinity by powder X-ray diffraction demonstrated that composition of the studied samples (S-3-1-B-TSA (hereinafter S3-1), S-3-2-B-HBr (S3-2), S-3-4-B-HCl (S3-4), S-3-8-B-HBr (S3-8), S-3-9-B-CSA (S3-9), S-3-10-B-HCl (S3-10), S-3-11-C2-HCl (S3-11), S-3-12-A1-TSA (S3-12), S-3-16-D-SA (S3-16) and S-3-17-D-MSA (S3-17)) included crystal phases. Various peak broadening and impossibility to characterize the diffraction patterns using a reflection of a phase with one unit cell was indicative of presence of several crystal phases in the studied samples (see FIGS. 4 to 8). The samples did not have similar crystal phases: peak positions and intensities were different in different samples. Size of crystallites in the S-3-17-D-MSA sample is low, lines are significantly broaden, which was probably resulted from destruction of the substance crystal structure (see FIG. 8). In the rest samples, percent of peaks with high crystallite size is higher.

The sample S-3-10-B-HCl is an individual crystal phase, however due to large line width and low reflection power of the sample, the assignment is ambiguous. The most probable parameters of a unit cell: a=10.99±0.05 Å; b=28.53±0.05 Å; c=10.62±0.05 Å; α=95.98±0.1°; β=95.85±0.1°; γ=92.74±0.1°. Space group P$\bar{1}$.

The sample S-3-11-C2-HCl is also a crystal phase and can also be assigned in different ways. Expected cell: a=10.36±0.05 Å; b=18.20±0.05 Å; c=28.08±0.05 Å; α=87.36±0.1°; β=87.54±0.1°; γ=92.29±0.1°. Space group P1.

The sample S-3-12-A1-TSA is an individual crystal phase with the following cell parameters: a=10.98±0.05 Å; b=28.48±0.05 Å and c=10.60±0.05 Å, β=113.7±0.1°, V=3,037.5±0.5 Å$^3$. Space group P2$_1$/c. A peak not related to a crystal phase is observed about 22.7° 2θ, it is related to a kapton base (see FIG. 9a). Table 2 shows position and intensity of visually differentiated intrinsic peaks in Debye diffraction pattern of the S-3-12-A1-TSA sample. FIG. 11a presents a general view of a unit cell independent part of 4-methylbenzenesulfonic acid and the Compound 1 salt hydrate in a polymorphic modification A (S-3-12-A1-TSA sample).

TABLE 2

The position and intensity of visually differentiated intrinsic peaks in Debye diffraction pattern of the 4-methylbenzenesulfonic acid and the Compound 1 base salt hydrate sample (polymorphic modification A). Intensities are the peak heights (adjusted to the background). Positions correspond to maxima at the Debye diffraction pattern, but not to the calculated position of reflections

| Peak position (2θ) | Relative intensity |
|---|---|
| 6.2 | 82.1 |
| 8.8 | 77.0 |
| 9.6 | 7.3 |
| 10.7 | 14.1 |
| 11.0 | 20.6 |
| 11.6 | 21.7 |
| 12.4 | 16.0 |
| 13.0 | 0.9 |
| 13.5 | 1.0 |
| 15.3 | 13.4 |
| 16.2 | 23.8 |
| 16.5 | 15.4 |
| 17.0 | 11.5 |
| 17.4 | 25.9 |
| 17.6 | 15.8 |
| 17.9 | 17.0 |
| 18.3 | 6.0 |
| 18.6 | 8.8 |
| 19.3 | 8.6 |
| 19.3 | 8.6 |
| 19.6 | 28.5 |
| 19.9 | 2.9 |
| 20.6 | 13.9 |

TABLE 2-continued

The position and intensity of visually differentiated intrinsic peaks in Debye diffraction pattern of the 4-methylbenzene-sulfonic acid and the Compound 1 base salt hydrate sample (polymorphic modification A). Intensities are the peak heights (adjusted to the background). Positions correspond to maxima at the Debye diffraction pattern, but not to the calculated position of reflections

| Peak position (2θ) | Relative intensity |
| --- | --- |
| 20.9 | 6.9 |
| 22.9 | 3.2 |
| 23.1 | 2.2 |
| 23.5 | 5.3 |
| 24.0 | 2.1 |
| 24.5 | 2.0 |
| *25.2* | *100* |
| *26.2* | *21.9* |
| *26.5* | *14.3* |
| 27.0 | 4.2 |
| *27.2* | *7.5* |
| *27.6* | *15.9* |
| 28.5 | 1.6 |
| 29.0 | 1.3 |
| 29.5 | 3.4 |
| *30.2* | *6.2* |
| 30.6 | 0.7 |
| 31.1 | 3.0 |
| 31.6 | 0.9 |
| 31.9 | 0.5 |
| 32.2 | 1.3 |
| 32.8 | 3.3 |
| 33.5 | 1.6 |
| 34.0 | 1.0 |
| 34.6 | 0.5 |
| 34.8 | 0.7 |
| 35.2 | 1.9 |
| 35.8 | 2.7 |
| 36.2 | 1.3 |
| 36.5 | 0.9 |
| 36.9 | 1.7 |
| 37.6 | 1.9 |
| 38.0 | 1.3 |
| 38.9 | 1.8 |
| 39.0 | 1.7 |
| 39.2 | 1.6 |
| 39.5 | 1.5 |
| 39.8 | 2.5 |
| 40.1 | 1.6 |
| 40.5 | 2.5 |
| 40.9 | 2.2 |
| 41.2 | 2.2 |
| 41.4 | 2.4 |
| 41.5 | 2.5 |
| 42.2 | 4.5 |
| 42.6 | 3.6 |
| 42.7 | 3.8 |
| 43.0 | 3.7 |
| 43.3 | 2.7 |
| 43.5 | 2.6 |
| 44.0 | 1.6 |
| 44.1 | 1.6 |
| 44.4 | 1.3 |
| 44.7 | 1.4 |
| 45.0 | 2.4 |
| 45.4 | 1.9 |
| 46.0 | 2.1 |
| 46.8 | 1.9 |
| 47.1 | 1.7 |
| 47.4 | 1.3 |
| 47.8 | 1.1 |
| 48.1 | 1.0 |
| 48.3 | 1.0 |
| 48.6 | 0.9 |
| 48.9 | 0.7 |
| 49.2 | 1.2 |
| 49.8 | 0.9 |
| 50.5 | 1.2 |
| 51.1 | 1.0 |
| 51.2 | 1.0 |
| 51.4 | 1.1 |
| 51.7 | 1.5 |
| 52.0 | 0.9 |
| 52.3 | 1.1 |
| 53.1 | 1.0 |
| 53.5 | 0.5 |
| 53.7 | 0.6 |
| 54.3 | 1.0 |
| 55.2 | 0.5 |
| 55.5 | 0.6 |
| 56.0 | 0.4 |
| 56.8 | 0.5 |
| 57.0 | 0.6 |
| 57.3 | 0.4 |

Note:
peaks with relative intensity exceeding 5.0 are shown in italics.

Thus, only three samples, S-3-10-B-HCl (S3-10), S-3-11-C2-HCl (S3-11) and S-3-12-A1-TSA (S3-12), are crystalline substances, and only the S-3-12-A1-TSA (S3-12) sample has a type of a space group, which is assigned unambiguously. Based on elemental analysis data, the S-3-12-A1-TSA sample is a monohydrate. To confirm the composition, the sample was analyzed using differential scanning calorimetry (DSC) and thermogravimetric analysis (TGA). DSC was carried out using NETZSCH DSC 204 F1 device. The measurement system was calibrated following ISO 11357-1 versus reference substance phase transition parameters ($C_6H_{12}$; Hg; benzoic acid; Ga; $KNO_3$; In; Sn; Bi; CsCl; purity 99.99%). A systematic error of temperature calibration (determined using In) makes 0.1°. The samples were tested in standard aluminum cells (V=56 mm$^3$, d=6 mm) crimped with a cap having a hole (ratio of cell bottom area to hole area was about 40) in a flow (20 ml/min) of synthetic air at temperatures within the range of 30° C. to 300° C. and a heating rate 10°/min. TGA measurements were carried out using NETZSCH TG 209 F1 thermobalance equipped with an alundum holder, protective screen and temperature sensor of P type. The device was calibrated versus reference substance melting points (Ag; Al; Bi; In; Sn; purity 99.99%). An error of weighing do not exceed 0.1% (determined versus $CaC_2O_1 \cdot 2H_2O$ reference substance). The experiment was carried out in a standard alundum container (V=85 mm$^3$, d=6.7 mm) in a flow of synthetic air at temperatures within the range of 30° C. to 300° C. and at a heating rate of 10°/min. Experimental data were processed using NETZSCH Proteus Analysis software suite following ISO/CD 11358 standard. The sample was weighed using AND GH 202 analytical balance having accuracy of ±0.01 mg. The material was not subjected to a mechanical treatment before measurements in order to avoid dehydration.

Figure 10:
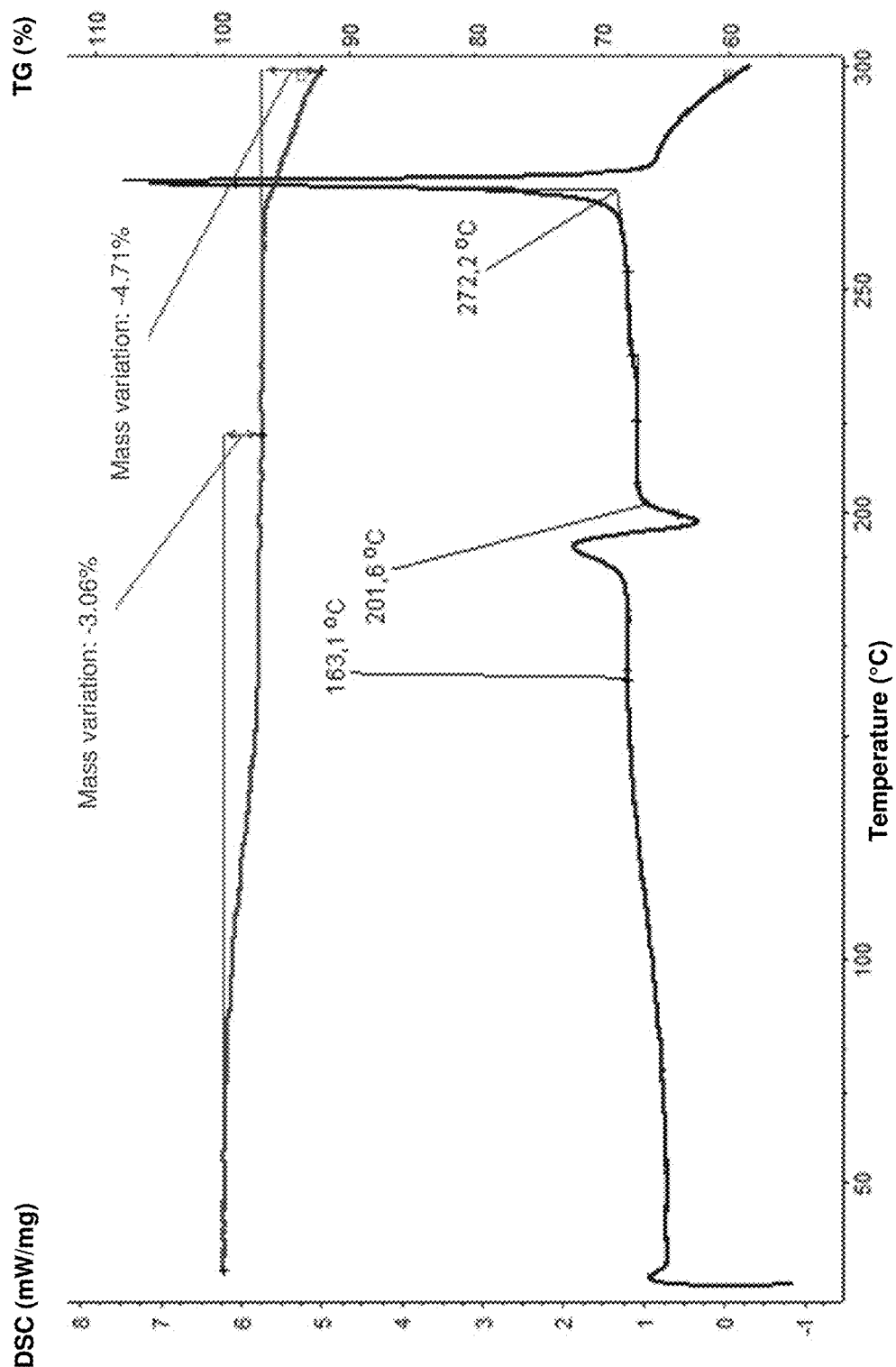
FIG. 10. Curves of TGA (thermogravimetric analysis) and DSC (differential scanning calorimetry) of 4-methylbenzenesulfonic acid and Compound 1 salt hydrate (S-3-12-A1-TSA sample, polymorphic modification A).

The results of the sample testing are given in FIG. 10. Initial weight loss and character of transitions corresponding to effects on DSC curves is in line with loss of crystal water. The last effect on DSC curves and correspondent weight loss are related to the sample melting followed by decomposition. This conclusion can be made based on visual observation of the studied sample final appearance.

Further studies of a thermal treatment effect on crystalline structure of 4-methylbenzenesulfonic acid and Compound 1 base salt hydrate showed that heating of the polymorphic modification A to 110-115° C. at residual pressure of 6 mbar within 2 hours results in changes of the salt crystalline structure and forming of the polymorphic modification B (SYK 91/1 sample). Further studies of sample crystallinity by powder X-ray diffraction demonstrated that the sample is an individual crystal phase with the following parameters of a unit cell: a=11.09±0.05 Å; b=14.38±0.05 Å and c=10.53±0.05 Å, α=90.06±0.1°; β=114.6±0.1° and γ=91.1±0.1°, V=1,525.9±0.5 Å$^3$ and space group P$\bar{1}$ (see FIG. 9b). Table 3 shows position and intensity of visually differentiated intrinsic peaks in Debye diffraction pattern of the SYK 91/1 sample. FIG. 11b presents a general view of a unit cell independent part of 4-methylbenzenesulfonic acid and the Compound 1 salt hydrate in a polymorphic modification B (sample SYK 91/1).

TABLE 3

The position and intensity of visually differentiated intrinsic peaks in Debye diffraction pattern of the 4-methylbenzenesulfonic acid and the Compound 1 base salt hydrate sample (polymorphic modification B). Intensities are the peak heights (adjusted to the background). Positions correspond to maxima at the Debye diffraction pattern, but not to the calculated position of reflections

| Peak position (2θ) | Relative intensity |
|---|---|
| *6.1* | *100* |
| *8.8* | *79.0* |
| 9.2 | 2.8 |
| 9.7 | 2.5 |
| *10.6* | *10.5* |
| *11.0* | *24.5* |
| *11.5* | *17.9* |
| *12.3* | *26.2* |
| *15.0* | *6.5* |
| *15.2* | *11.5* |
| *15.5* | *9.5* |
| *15.8* | *7.9* |
| *16.1* | *29.1* |
| *16.3* | *40.0* |
| *17.3* | *29.8* |
| *17.6* | *24.2* |
| *17.9* | *23.1* |
| *18.5* | *22.6* |
| *19.5* | *32.2* |
| *20.5* | *11.8* |
| *20.7* | *11.7* |
| *20.8* | *11.8* |
| 21.2 | 2.9 |
| 21.8 | 1.8 |
| 22.2 | 2.3 |
| 23 | 1.5 |
| 23.2 | 2.1 |
| 23.8 | 4.2 |
| *24.6* | *5.9* |
| *24.8* | *9.4* |
| *25.1* | *93.3* |
| *26.1* | *7.2* |
| *26.5* | *20.1* |
| *26.9* | *11.0* |
| 27.4 | 3.8 |
| 27.9 | 1.2 |
| 29.0 | 2.4 |
| 29.4 | 3.4 |
| *30.1* | *11.8* |
| 30.6 | 1.7 |
| 30.9 | 1.5 |
| 31.1 | 1.5 |
| 31.4 | 1.5 |
| 31.7 | 1.9 |
| 31.9 | 2.2 |
| 32.5 | 2.9 |
| 32.9 | 2.1 |
| 33.2 | 2.2 |
| 33.5 | 2.1 |
| 33.8 | 1.2 |
| 34.4 | 0.9 |
| 34.7 | 1.8 |
| 35.1 | 2.1 |
| 35.6 | 2.2 |
| 35.8 | 1.8 |
| 36.4 | 1.5 |
| 36.6 | 1.3 |
| 37.0 | 1.4 |
| 37.5 | 3.1 |
| 38.0 | 1.7 |
| 38.8 | 2.6 |
| 39.1 | 1.5 |
| 39.4 | 2.2 |
| 39.6 | 1.5 |
| 39.9 | 1.6 |
| 40.1 | 1.7 |
| 40.4 | 2.0 |
| 40.6 | 2.3 |
| 41.3 | 3.1 |
| 42.1 | 4.3 |
| 42.6 | 4.8 |
| 43.0 | 5.9 |
| 44.0 | 1.9 |
| 44.5 | 1.4 |
| 45.0 | 2.2 |
| 46.0 | 2.2 |
| 46.8 | 1.7 |
| 47.3 | 2.2 |
| 47.5 | 2.2 |
| 48.0 | 2.0 |
| 48.4 | 1.6 |
| 49.5 | 2.1 |
| 50.0 | 2.3 |
| 50.2 | 2.1 |
| 50.8 | 1.9 |
| 51.6 | 3.0 |
| 52.1 | 1.9 |
| 52.7 | 2.0 |
| 53.5 | 1.4 |
| 54.1 | 1.0 |
| 55.2 | 0.4 |

Note:
peaks with relative intensity exceeding 5.0 are shown in italics.

Based on the conducted study, it was established that 4-methylbenzenesulfonic acid and the Compound 1 salt is the only crystal salt form of the Compound 1, which can be produced in low-toxic organic solvents using an easily scalable method, and which contains a pharmacologically acceptable counterion.

Analysis of Impurities

In Various Compound 1 Salt Forms

Analysis of impurities content in various salt forms was carried out to evaluate quality of the obtained Compound 1 salt forms. The impurities were determined by HPLC method. Content of a single impurity was calculated irrespective of area of peaks correspondent to peaks in blank chromatogram in terms of retention time and to counterion peak. Total impurity content was calculated by summing up results of single impurities.

A HPLC procedure for impurity measurement was developed at the first stage of the study. Then samples of a free base and several salt forms of the Compound 1 were analyzed for impurities. The results of the studies are presented in FIGS. 15 to 17 and in Tables 4 to 7.

TABLE 4

The results of the Compound 1 (free base) sample analysis for impurities

| Peak No. | Retention time, min | Area, mAU*, min. | Height, mAU | Width, min. | Area, % | Symmetry |
|---|---|---|---|---|---|---|
| 1 | 3.061 | 50.7 | 8.5 | 0.0993 | 1.036 | 1.085 |
| 4 | 10.699 | 15.9 | 1.7 | 0.1584 | 0.325 | 1.007 |
| 7 | 15.693 | 7.2 | 1.1 | 0.1104 | 0.148 | 0.97 |
| 12 | 21.156 | 4,773.3 | 515.1 | 0.1545 | 97.488 | 0 |
| 16 | 25.207 | 25.5 | 2.7 | 0.1594 | 0.521 | 1.018 |

Note:
*mAU—milli-absorbance units;
Peak 12 is a peak of 2,2-dimethyl-6-((4-((3,4,5-trimethoxyphenyl)amino)-1,3,5-triazine-2-yl)amino)-2H-pyrido[3,2-b][1,4]oxazine-3(4H)-one.

TABLE 5

The results of the methanesulfonic acid and Compound 1 salt sample analysis for impurities

| Peak No. | Retention time, min | Area, mAU*, min. | Height, mAU | Width, min. | Area, % | Symmetry |
|---|---|---|---|---|---|---|
| 1 | 2.979 | 43.4 | 8.30 | 0.0868 | 0.922 | 0.812 |
| 2 | 9.110 | 10.7 | 0.56 | 0.3172 | 0.228 | 0.435 |
| 3 | 10.632 | 19.2 | 2.00 | 0.1611 | 0.408 | 0.989 |
| 8 | 16.301 | 5.4 | 0.80 | 0.1119 | 0.115 | 1.383 |
| 12 | 21.123 | 4,573.5 | 494.40 | 0.1542 | 97.249 | 2.2 |
| 17 | 25.177 | 26.6 | 2.70 | 0.164 | 0.566 | 1.024 |
| 18 | 27.138 | 6.8 | 0.81 | 0.1402 | 0.145 | 0.963 |

Note:
*mAU—milli-absorbance units;
Peak 12 is a peak of 2,2-dimethyl-6-((4-((3,4,5-trimethoxyphenyl)amino)-1,3,5-triazine-2-yl)amino)-2H-pyrido[3,2-b][1,4]oxazine-3(4H)-one.

TABLE 6

The results of the 4-methylbenzenesulfonic acid and Compound 1 salt hydrate (polymorphic modification A) sample analysis for impurities

| Peak No. | Retention time, min | Area, mAU*, min. | Height, mAU | Width, min. | Area, % | Symmetry |
|---|---|---|---|---|---|---|
| 1 | 13.721 | 0.9 | 0.10 | 0.1524 | 0.025 | 2.009 |
| 2 | 14.02 | 0.8 | 0.09 | 0.1411 | 0.02 | 2.831 |
| 3 | 14.421 | 3.7 | 0.76 | 0.0844 | 0.098 | 0.996 |
| 4 | 14.837 | 1.0 | 0.17 | 0.1014 | 0.027 | 1.316 |
| 5 | 15.079 | 3.2 | 0.48 | 0.1125 | 0.085 | 0.923 |
| 6 | 15.382 | 0.3 | 0.07 | 0.074 | 0.008 | 1.198 |
| 7 | 16.326 | 2.7 | 0.26 | 0.1726 | 0.073 | 0.378 |
| 8 | 18.061 | 1.0 | 0.14 | 0.1258 | 0.027 | 0.935 |
| 9 | 21.156 | 3,749.6 | 423.30 | 0.1476 | 99.573 | 1.955 |
| 10 | 27.175 | 2.2 | 0.27 | 0.137 | 0.058 | 0.981 |

Note:
*mAU—milli-absorbance units;
Peak 9 is a peak of 2,2-dimethyl-6-((4-((3,4,5-trimethoxyphenyl)amino)-1,3,5-triazine-2-yl)amino)-2H-pyrido[3,2-b][1,4]oxazine-3(4H)-one.

TABLE 7

The results of the 4-methylbenzenesulfonic acid and Compound 1 salt hydrate (polymorphic modification B) sample analysis for impurities

| Peak No. | Retention time, min | Area, mAU*, min. | Height, mAU | Width, min. | Area, % | Symmetry |
|---|---|---|---|---|---|---|
| 1 | 13.727 | 0.6 | 0.10 | 0.095 | 0.014 | 0.824 |
| 2 | 14.01 | 1.1 | 0.13 | 0.1445 | 0.029 | 2.454 |
| 3 | 14.423 | 3.6 | 0.66 | 0.0911 | 0.092 | 0.894 |
| 4 | 14.827 | 0.5 | 0.08 | 0.1016 | 0.013 | 1.616 |
| 5 | 15.035 | 2.3 | 0.36 | 0.1041 | 0.057 | 0.938 |
| 6 | 15.374 | 0.5 | 0.08 | 0.096 | 0.012 | 1.2 |
| 7 | 16.302 | 2.5 | 0.33 | 0.1255 | 0.063 | 6,905.67 |
| 8 | 16.457 | 0.7 | 0.14 | 0.0784 | 0.017 | 0.787 |
| 9 | 17.588 | 0.6 | 0.09 | 0.1234 | 0.016 | 0.88 |
| 10 | 18.026 | 0.6 | 0.09 | 0.1163 | 0.016 | 0.833 |
| 11 | 21.145 | 3,921.8 | 435.80 | 0.15 | 99.599 | 0 |
| 12 | 22.079 | 0.6 | 0.07 | 0.1334 | 0.015 | 0 |

Note:
*mAU—milli-absorbance units;
Peak 11 is a peak of 2,2-dimethyl-6-((4-((3,4,5-trimethoxyphenyl)amino)-1,3,5-triazine-2-yl)amino)-2H-pyrido[3,2-b][1,4]oxazine-3(4H)-one.

As the result of the analysis for impurities in the sample of Compound 1 in a form of a free base, high content of various unidentified impurities was found in the samples; this impurity content can provoke toxic effects and adverse events as the result of this compound introducing as a drug into a human or animal body. Therefore, additional purification stages are required to use the Compound 1 as a drug candidate. The additional purification stages would inevitably result in a more complicated process flow and increase of final drug production cost price.

As the result of the analysis for impurities in the sample of methanesulfonic acid and Compound 1 salt, somewhat lower content of various unidentified impurities was found as compared to impurity content in a free base (Compound 1). However, as it is seen in FIG. 16 and Table 5, content of two impurities exceed 0.5%. Despite of the fact that such impurity content is acceptable for drug production according to the requirements of ICH (International Conference on Harmonization) and Russian regulatory documents, this high concentration of impurities can lead to toxic effects at administration in a human or animal body; therefore use of such salt in clinical practice is possible only based on the results of this impurity toxicity studies and/or additional stages of the salt purification.

The analysis of impurities in the sample of 4-methylbenzenesulfonic acid and Compound 1 salt hydrate unexpectedly showed no impurities exceeding 0.1%. It should be noted, when low quality 4-methylbenzenesulfonic acid is used, the 4-methylbenzenesulfonic acid and free base salt hydrate can contain up to 0.15% of ortho-toluenesulfonic acid, however, this impurity is easily removed by recrystallization of 4-methylbenzenesulfonic acid. According to regulatory documents, such low concentrations (below 0.1%) of impurities are considered safe and do not require identification of impurity structures or additional purification stages.

Thus, the analysis of impurities in the samples of various Compound 1 salt forms unexpectedly showed that 4-methylbenzenesulfonic acid and Compound 1 salt hydrate has the highest purity among the studied salts and contains no impurities exceeding 0.15%.

Characteristics of Biological Activity of Compounds According to the Invention Various experiments were carried out to study biological activity of 4-methylbenzenesulfonic acid and Compound 1 salt and crystalline forms thereof being the object of this invention.

Study of 4-methylbenzenesulfonic Acid and Compound 1 Salt Effect on Human Kinase Enzymatic Activity In Vitro The studies of effect of the compounds according to the invention on human kinase enzymatic activity in vitro for the first time revealed a direct inhibition effect of 4-methylbenzenesulfonic acid and Compound 1 salt (as a polymorphic modification A) on a range of human recombinant tyrosine kinases, particularly on human c-Src tyrosine kinase.

The Compound 1 effect on the human recombinant tyrosine c-Src kinase was measured as follows: a peptide substrate was dissolved in a reaction buffer ad 0.2 mg/ml concentration. A solution of recombinant c-Src kinase was added to 2 nM concentration and the studied compound to the required concentration (within the range of 1 nM to 10 µM) was added. A solution of $^{33}$P-ATP was added to 10 µM concentration (final specific activity of the solution is 0.01 µCi). After 120 minutes of incubation, the reaction mixture was applied on ion-exchange paper, which was rinsed with a plenty of phosphoric acid. A reaction extent was determined based on radioactivity of the reaction products.

The conducted studies showed that 4-methylbenzenesulfonic acid and Compound 1 salt at concentration of 0.5 µmol/l inhibits activity of the following kinases for more than 50%: Blk, c-Src, Syk, Fgr, Frk, Fyn, Hck, Lck, Lyn, Yes. The most significant inhibition of catalytic activity was detected for Src-kinase family; the effect of 4-methylbenzenesulfonic acid and Compound 1 salt at concentration of 0.5 µmol/l reduces residual Src-kinase family activity to 25% and lower of control values. Particularly, the residual activity of c-Src kinase in presence of 4-methylbenzenesulfonic acid and Compound 1 salt at concentration of 0.5 µmol/l made 6% of control values, the residual activity was 12% of Yes and Lck kinases, 13% of Lyn kinase, 20 of Blk, 23% of Fgr, 25% of Fyn and Hck kinases.

Figure 12:
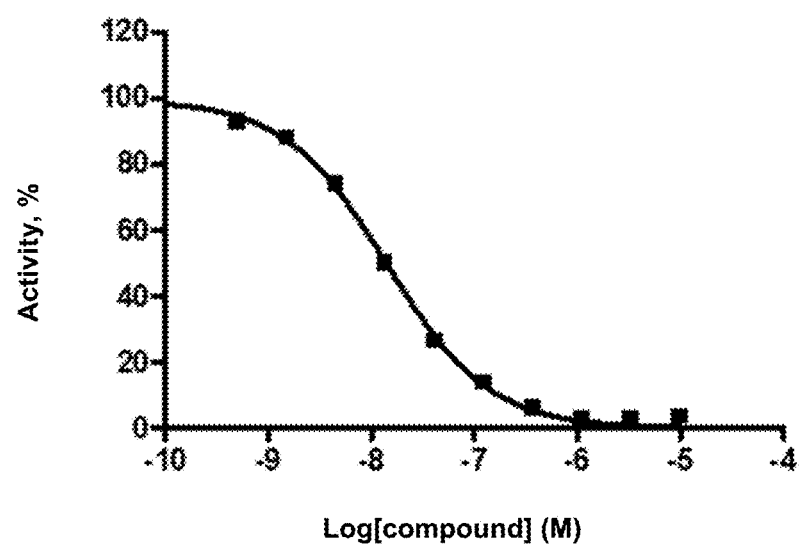
FIG. 12. Influence of 4-methylbenzenesulfonic acid and Compound 1 salt hydrate (polymorphic modification A) on human c-Src kinase activity.

Concentrations of half-maximum inhibition ($IC_{50}$) of kinase enzymatic activity were determined to refine the obtained data. As the result, an inhibition effect of 4-methylbenzenesulfonic acid and Compound 1 salt on the human recombinant tyrosine kinase c-Src (see FIG. 12) was demonstrated in a nanomolar range of concentrations ($IC_{50}$=14 nmol/l). Furthermore, 4-methylbenzenesulfonic acid and Compound 1 salt also inhibits Syk kinase in the nanomolar range of concentrations ($IC_{50}$=40 nmol/l).

Comparison of Pharmacokinetics of Free Base and Compound I Salt Forms

Pharmacokinetic parameters of the obtained Compound 1 salt forms were studied to evaluate suitability thereof as drugs.

At the first stage, pharmacokinetics of the Compound 1 free base was studied after oral administration in Wistar rats at dosage of 30 mg/kg. The study results are given in FIG. 19 and Table 9. As the presented results show, a maximum concentration of the substance in plasma makes 4.12 ng/ml which is correspondent to 9.1 nmol/l, and average daily concentration of the substance makes 4.8 nmol/l. At the same time, the studies of Compound 1 biological activity showed that effective concentration of the free base makes about 1 µmol/l. Therefore, the pharmacokinetic parameters of the free base eliminate its use as a drug since a high dosage of the Compound 1 is required to achieve the required therapeutic effect. This would be rather impractical for technical and practical implementation, would lead to significant substance consumption and would also lead to the onset of toxic gastrointestinal adverse events.

TABLE 9

The basic pharmacokinetic parameters of the Compound 1 at administration as a free base to Wistar rats at a dose of 30 mg/kg. Average values for each time point are determined based on individual data received in three animals

| $T_{1/2}$ (h) | $T_{max}$ (h) | $C_{max}$ (ng/ml) | $AUC_{0-t}$ (ng · h/ml) | $AUC_0$-∞ (ng · h/ml) | Vz(/F) (l/kg) | CL(/F) (l/h/kg) |
|---|---|---|---|---|---|---|
| 11.82 | 4 | 4.12 | 55 | 73 | 6,982.6 | 409.5 |

Pharmacokinetics of several Compound 1 salt forms was studied after oral administration in Wistar rats at a dose of 37 mg/kg (30 mg/kg equivalent to a free base). FIG. 20 and Table 10 show results of the pharmacokinetics study of methanesulfonic acid and Compound 1 salt. As the presented results show, the methanesulfonic acid and Compound 1 salt has significantly more favorable pharmacokinetic parameters versus the free base. A maximum concentration of the substance in plasma makes 333 ng/ml which is correspondent to 735 nmol/l, and average daily concentration of the substance makes 104 nmol/l. At the same time, the studies of Compound 1 biological activity showed that effective concentration of the Compound 1 makes about 1 µmol/l. Therefore, a significantly higher substance dosage or multiple-dose administration is required to use the methanesulfonic acid and Compound 1 salt as a drug.

TABLE 10

The basic pharmacokinetic parameters of the methanesulfonic acid and Compound 1 salt at administration to Wistar rats at a dose of 30 mg/kg (equivalent to a free base). Average values for each time point are determined based on individual data received in three animals

| $T_{1/2}$ (h) | $T_{max}$ (h) | $C_{max}$ (ng/ml) | $AUC_{0-t}$ (ng · h/ml) | $AUC_0$-∞ (ng · h/ml) |
|---|---|---|---|---|
| 3.0 | 0.5 | 333 | 1,130 | 1,144 |

The pharmacokinetics study of 4-methylbenzenesulfonic acid and Compound 1 salt hydrate after oral administration to Wistar rats unexpectedly showed that this salt form has the optimal pharmacokinetics parameters versus the free base and other studied salt forms of the Compound 1. FIG. 21 and Table 11 show results of the pharmacokinetics study of 4-methylbenzenesulfonic acid and Compound 1 salt hydrate. When 4-methylbenzenesulfonic acid and Compound 1 salt hydrate was administered to Wistar rats at a dose of 30 mg/kg (21 mg/kg equivalent to a free base), a maximum concentration of the substance in plasma made 416 ng/ml, which is correspondent to about 1 µmol/l, and average daily concentration of the substance exceeded 200 nmol/l.

TABLE 11

The basic pharmacokinetic parameters of the 4-methyl-
benzenesulfonic acid and Compound 1 salt hydrate (polymorphic
modification A) at administration to Wistar rats at a dose
of 21 mg/kg (equivalent to a free base). Average values for
each time point are determined based on individual data
received in six animals

| $T_{1/2}$ (h) | $T_{max}$ (h) | $C_{max}$ (ng/ml) | $AUC_{0-t}$ (ng · h/ml) | $AUC_0·\infty$ (ng · h/ml) |
|---|---|---|---|---|
| 5.0 | 1.5 | 416 | 2,339 | 2,418 |

Further pharmacokinetics studies of 4-methylbenzenesulfonic acid and Compound 1 salt hydrate in rats showed that the drug is rapidly absorbed into the blood reaching maximum concentration after 1.1 to 1.3 hours and distributed across organs and tissues. Daily average concentration of the substance in bone and cartilage tissues exceeds daily average concentration of the substance in animal blood plasma more than three times. 4-methylbenzenesulfonic acid and Compound 1 salt hydrate has a linear pharmacokinetics within a wide range of doses. When the 4-methylbenzenesulfonic acid and Compound 1 salt hydrate is administered intragastrically at dosages 30 to 200 mg/kg, the Compound 1 concentration in rat blood plasma increases in proportion to the dose. High concentrations of the Compound 1 was found almost in all the tissues studied and reached maximum at 2 to 4 hours after 4-methylbenzenesulfonic acid and Compound 1 salt hydrate administration. Daily average concentration of the Compound 1 in target organs (bone and cartilage tissues) exceeds daily average concentration of Compound 1 in animal blood plasma more than three times. The lowest concentration of the Compound 1 was registered in muscles.

Pharmacokinetics studies of 4-methylbenzenesulfonic acid and Compound 1 salt hydrate in rabbits at single administration at a dose of 50 mg/kg demonstrated that the concentration of the substance in the rabbit blood plasma reaches 8.6 μg/ml (~16 μmol/l), and elimination half-time makes more than 7 hours.

The pharmacokinetics studies of various Compound 1 salt forms unexpectedly showed that 4-methylbenzenesulfonic acid and Compound 1 salt is an optimal salt form of the Compound 1 allowing single oral administration at a significantly lower dose versus other studied salt forms of the Compound 1.

Study of 4-methylbenzenesulfonic Acid and Compound 1 Salt Hydrate Effect on Osteoclast-Mediated Resorption of Bone Tissue This experiment first time revealed an effect of 4-methylbenzenesulfonic acid and Compound 1 salt hydrate (polymorphic modification A) on osteoclast-mediated resorption of bone tissue. The study was carried out following the method below: CD15+ monocytes (osteoclast precursor cells) were cultivated for 3 days in a proliferation medium (Igla α-modified minimum essential medium/fetal calf serum (aMEM/FCS), 10% with 25 ng/ml of macrophage colony-stimulating factor (M-CSF)). During this stage M-CSF promoted proliferation and expression of a receptor activator of nuclear factor κB (RANK, cappa-B, type I membrane protein). The proliferation medium was removed and cells were differentiated in a differentiation medium (aMEM/FCS-10% with 100 ng/ml of RANKL and 25 ng/ml of M-CSF). When mature osteoclasts were detected in the culture (day 4 of the study), the cells were collected and re-inoculated into a 96-well plate coated with a synthetic mineralized matrix. Cultivation continued for 48 hours (at presence of the studied compounds) to evaluate osteoclast resorption. Then number of mature osteoclasts and the resorption degree were evaluated. An effect of 4-methylbenzenesulfonic acid and Compound 1 salt concentration on concentration and resorption degree of mature osteoclasts was evaluated in comparison with control samples (positive control, 0.3% DMSO solvent) and reference inhibitors, i.e., saracatinib and bosutinib (see FIG. 18). Similar values of average number of mature osteoclasts per well (488±43 and 451±11) and average degrees of mineralized matrix resorption (32.62±1.16% and 35.53±2.40%) in control samples (positive control, solvent) confirmed that the solvent did not have effect on osteoclast survival and osteoclast-mediated resorption. The conducted studies demonstrated that the Compound 1 has a dose-dependent inhibitory effect on the osteoclast-mediated resorption of the mineralized matrix. A profound statistically significant inhibitory effect was found at concentrations of 1.1 μM and 10 μM of 4-methylbenzenesulfonic acid and Compound 1 salt monohydrate (see FIG. 18).

A statistically significant dose-dependent inhibitory effect on the osteoclast-mediated resorption of the mineralized matrix was also found when 4-methylbenzenesulfonic acid and Compound 1 salt hydrate as a polymorphic modification B was used at concentrations from 1.0 μM.

Study of 4-methylbenzenesulfonic Acid and Compound 1 Salt Hydrate Effect on Cartilage Metabolism An effect of 4-methylbenzenesulfonic acid and Compound 1 salt was first time demonstrated using 4-methylbenzenesulfonic acid and Compound 1 salt monohydrate (polymorphic modification A). The study was carried out following the method below: chondrocytes were isolated from a knee joint cartilage of young rats (aged 3 weeks, Sprague Dawley line). The isolated chondrocytes in a cultural medium (Dulbecco's modified Igla minimum essential medium/fetal calf serum (DMEM/FCS), 10%, 4-(2-hydroxyethyl)-1-piperazine ethanesulfonic acid (HEPES), 25 mM) was stored frozen at −80° C. The obtained chondrocytes were unfrozen a day before the experiment, inoculated into 12-well plates and cultured as a monolayer during 24 hours. After 24 hours of incubation IL-1β-induced activation of chondrocytes and treatment with the studied compounds was started and continued for 3 days.

The conducted studies showed that 4-methylbenzenesulfonic acid and Compound 1 salt hydrate (polymorphic modification A) demonstrates a statistically significant positive effect on IL-1β-induced hypertrophic changes in chondrocytes manifested as significant increase in aggrecan expression.

Thus, based on the conducted studies results, an apparent protective effect of 4-methylbenzenesulfonic acid and Compound 1 salt on bone and cartilage tissues was found. These effects can be achieved only by using the Compound 1 salt forms having satisfactory pharmacokinetic parameters. It was found that pharmacokinetic parameters of the Compound 1 free base would not allow using this compound for arresting the osteoclast-mediated metabolism of bone tissue and IL-1β-induced hypertrophic changes in chondrocytes. At the same time 4-methylbenzenesulfonic acid and Compound 1 salt, particularly its monohydrate, has appropriate pharmacokinetic parameters and can be used for treatment of the diseases associated with aberrant bone and cartilage metabolism.

Study of 4-methylbenzenesulfonic Acid and Compound 1 Salt Effect on Destruction of a Knee Joint in Rat Models of Osteoarthritis Induced by Intra-Articular Introduction of Sodium Iodoacetate The studies conducted in animals demonstrated a direct pharmacological effect of 4-methylbenzenesulfonic acid and g. The test was repeated five times for each filament at intervals of 1 to 2 s. The sensitivity threshold was considered as a minimum reaction threshold provoking paw withdrawal in one of five repeats.

Table 8 contains the results of evaluation of effect of 4-methylbenzenesulfonic acid and Compound 1 salt monohydrate (polymorphic modification A) administration on destruction of a knee joint in rat models of osteoarthritis induced by intra-articular introduction of sodium iodoacetate.

TABLE 8

The study of pain sensitivity of affected extremities of animals using mechanical allodynia test with von Frey filaments. Presented value are minimum reaction threshold provoking affected paw withdrawal, in percents of reaction threshold value before the pathology induction (n = 10, M ± m)

| Group No. | Pathology Induction | Drug [administration route] | Dose, mg/kg | Days of drug administration | Days from pathology induction ||| 
|---|---|---|---|---|---|---|---|
| | | | | | 14 | 21 | 28 |
| | | | | | Reaction threshold value, % of control |||
| 1 | Distilled water | Solvent [intragastric] | 0 | 0-28 (daily) | 101 | 117 | 118 |
| 2 | Sodium iodoacetate | Solvent [intragastric] | 0 | 0-28 (daily) | 60 | 58 | 60 |
| 3 | | Salt monohydrate of 4-methylbenzenesulfonic acid and the Compound 1 [intragastric] | 100 | 0-28 (daily) | 106 | 80 | 106 |
| 4 | | | 500 | 0-28 (daily) | 114 | 106 | 107 |
| 5 | | | 100 | 7-28 (daily) | 70 | 75 | 73 |
| 6 | | | 500 | 7-28 (daily) | 76 | 91 | 118 |
| 7 | | Zoledronic acid [subcutaneously] | 0.1 | 0, 3, 6, 9, 12, 15, 18, 21, 24, 27 | 98 | 108 | 118 |
| 8 | | Naproxen [intragastric] | 50 | 14, 21, 28 | 82 | 102 | 96 |

Compound 1 salt as 4-methylbenzenesulfonic acid and Compound 1 salt monohydrate (polymorphic modification A) on destruction of a knee joint in Sprague-Dawley rat models of osteoarthritis induced by intra-articular introduction of sodium iodoacetate. The intra-articular introduction of aerobic glycolysis inhibitor (sodium iodoacetate) results in death of chondrocytes and acute inflammatory reaction in a synovial cavity. In absence of treatment, at day 10 from the pathology induction an onset of chronic pain is observed due to cartilage destruction and development of chronic inflammation in particular cases [J Musculoskel Neuron Interact 2001; 1(4):363-376]. Extent of osteoarthritis development in rats was evaluated by comparison of extremity pain sensitivity threshold after the introduction of sodium iodoacetate versus background measurements taken before the pathology induction. The threshold of the pain sensitivity was evaluated by mechanical allodynia test using von Frey filaments (see Table 8).

For the purposes of the study, rat males weighing 150 to 200 g were selected. All the animals underwent acclimatization for 14 days. The animals were housed in a polycarbonate cages of 3H type manufactured by Charles River laboratories Inc according to COST R 53434-2009. 12-hours lighting regimen was maintained. The animals had access to food and water ad libitum. The pathology was induced by introduction of 50 μl solution containing 2 mg of sodium iodoacetate into a synovial cavity of the animal knee joints. Tactile allodynia induced by a mechanical irritation was evaluated using von Frey filaments weighing 0.06 to 23.96

Total arrest of mechanical allodynia onset is achieved by administration of 4-methylbenzenesulfonic acid and Compound 1 salt hydrate at a dose of 100 and 500 mg/kg beginning at day of the pathology induction and at a dose of 500 mg/kg beginning at the seventh day of the pathology induction. Based on the conducted experiment it can be concluded that this compound inhibits aberrant bone and cartilage metabolism, and this in turn results in arrest of mechanical allodynia development and decrease of the pain sensitivity threshold in rat models of osteoarthritis.

Thus, the conducted experiments showed that 4-methylbenzenesulfonic acid and Compound 1 salt as well as its hydrate (monohydrate in particular), solvate, and polymorphic modifications of the salt, hydrate or solvate are effective inhibitors of Syk kinase and Src-kinase family, particularly c-Src kinase, and have pharmacokinetic parameters allowing use of the specified salts as a drug for introduction into a human or animal body to treat diseases associated with aberrant kinase activity leading to aberrant bone and cartilage metabolism, particularly osteoarthritis, osteoporosis and osteochondrosis.

Notwithstanding the invention is described with reference to disclosed embodiments, it should be apparent for the experts in this field that particular detailed experiments are given only for the purposes of this invention illustration, and they shall not be considered as somehow limiting the scope of the invention. It should be apparent, that various modifications are possible without a departure from the essence of this invention.

The invention claimed is:

1. A salt of 4-methylbenzenesulfonic acid and 2,2-dimethyl-6-((4-((3,4,5-trimethoxyphenyl)amino)-1,3,5-triazine-2-yl)amino)-2H-pyrido[3,2-b][1,4]oxazine-3 (4H)-one base:

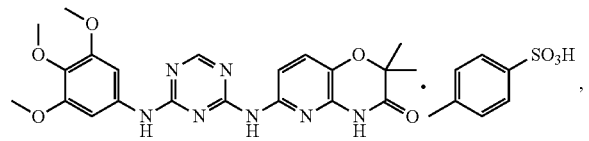, its hydrate, solvate or polymorphic modification of the salt, hydrate or solvate.

2. A salt of 4-methylbenzenesulfonic acid and 2,2-dimethyl-6-((4-((3,4,5-trimethoxyphenyl)amino)-1,3,5-triazine-2-yl)amino)-2H-pyrido[3,2-b][1,4]oxazine-3(4H)-one base:

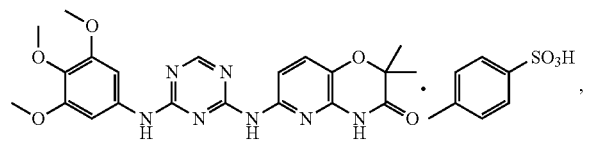

or a hydrate thereof or polymorphic modification of the salt or hydrate thereof.

3. A salt according to claim 2 which hydrate polymorphic modification is a crystal phase featured with the following parameters of a unit cell: a=10.98±0.05 Å, b=28.48±0.05 Å, c=10.60±0.05 Å, β=113.7±0.1°, V=3,037.5±0.5 Å³; space group P2₁/c.

4. A salt according to claim 2 which hydrate polymorphic modification is a crystal phase featured with intrinsic peaks in Debye diffraction pattern at diffraction angles (2θ) 6.2; 8.8; 9.6; 10.7; 11.0; 11.6; 12.4; 15.3; 16.2; 16.5; 17.0; 17.4; 17.6; 17.9; 18.3; 18.6; 19.3; 19.3; 19.6; 20.6; 20.9; 23.5; 25.2; 26.2; 26.5; 27.2; 27.6 and 30.2, obtained by a powder X-ray diffraction method at temperature of 25±5° C. using CuKα1 radiation at wave length of 1.5406 Å.

5. A salt according to claim 2 which hydrate polymorphic modification is a crystal phase featured with the following parameters of a unit cell: a=11.09±0.05 Å, b=14.38±0.05 Å, c=10.53±0.05 Å, α=90.06±0.1°, β=114.6±0.1°, γ=91.1±0.1°, V=1,525.9±0.5 Å³; space group P1.

6. A salt according to claim 2 which hydrate polymorphic modification is a crystal phase featured with intrinsic peaks in Debye diffraction pattern at diffraction angles (2θ) 6.1; 8.8; 10.6; 11.0; 11.5; 12.3; 15.0; 15.2; 15.5; 15.8; 16.1; 16.3; 17.3; 17.6; 17.9; 18.5; 19.5; 20.5; 20.7; 20.8; 24.6; 24.8; 25.1; 26.1; 26.5; 26.9; 30.1 and 43.0, obtained by a powder X-ray diffraction method at temperature of 25±5° C. using CuKα1 radiation at wave length of 1.5406 Å.

7. The pharmaceutical composition for prevention and/or treatment of a disorder related to aberrant kinase activity and containing therapeutically effective amount of a salt of 4-methylbenzenesulfonic acid and 2,2-dimethyl-6-((4-((3,4,5-trimethoxyphenyl)amino)-1,3,5-triazine-2-yl)amino)-2H-pyrido[3,2-b][1,4]oxazine-3(4H)-one base:

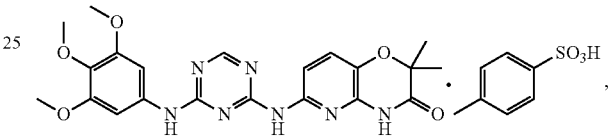, or hydrate thereof, a solvate thereof, or polymorphic modification of the salt, hydrate thereof, or solvate thereof and at least one pharmaceutically acceptable auxiliary substance.

8. The pharmaceutical composition according to claim 7 featured with an auxiliary substance being a carrier and/or excipient.

* * * * *